United States Patent
Raichle et al.

(10) Patent No.: US 8,546,295 B2
(45) Date of Patent: Oct. 1, 2013

(54) PROCESS FOR PREPARING SHAPED CATALYST BODIES WHOSE ACTIVE COMPOSITION IS A MULTIELEMENT OXIDE

(75) Inventors: Andreas Raichle, Ludwigshafen (DE); Frank Rosowski, Mannheim (DE); Sabine Huber, Limburgerhof (DE); Ulrich Cremer, Mannheim (DE); Stefan Altwasser, Wachenheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1396 days.

(21) Appl. No.: 12/015,741

(22) Filed: Jan. 17, 2008

(65) Prior Publication Data
US 2008/0177105 A1  Jul. 24, 2008

Related U.S. Application Data

(60) Provisional application No. 60/886,757, filed on Jan. 26, 2007, provisional application No. 60/885,701, filed on Jan. 19, 2007.

(30) Foreign Application Priority Data

Jan. 19, 2007  (DE) .......................... 10 2007 003 778
Jan. 26, 2007  (DE) .......................... 10 2007 004 961

(51) Int. Cl.
*B01J 23/00* (2006.01)
*C07C 51/16* (2006.01)

(52) U.S. Cl.
USPC ............................ 502/311; 562/546; 562/547

(58) Field of Classification Search
USPC .................................. 562/546, 547; 502/311
See application file for complete search history.

(56) References Cited

U.S. PATENT DOCUMENTS

| | | | |
|---|---|---|---|
| 4,764,498 A | 8/1988 | Wissner et al. | |
| 5,173,468 A | 12/1992 | Boehning et al. | |
| 5,221,767 A | 6/1993 | Boehning et al. | |
| 5,773,382 A | 6/1998 | Mitchell et al. | |
| 6,383,976 B1 * | 5/2002 | Arnold et al. | 502/311 |
| 6,812,351 B2 | 11/2004 | Weiguny et al. | |
| 6,958,414 B2 | 10/2005 | Schliephake et al. | |

(Continued)

FOREIGN PATENT DOCUMENTS

| | | |
|---|---|---|
| DE | 103 53 014 A1 | 6/2004 |
| DE | 103 60 396 A1 | 7/2005 |

(Continued)

OTHER PUBLICATIONS

"Verfahren zur Herstellung von Katalysatorformkörpern, deren Aktivmasse ein Multielementoxid ist", Research Disclosure, Research Disclosure Database No. 497012, Published in Sep. 2005, 72 pages (with partial English translation).

(Continued)

*Primary Examiner* — Taylor Victor Oh
(74) *Attorney, Agent, or Firm* — Oblon, Spivak, McClelland, Maier & Neustadt, L.L.P.

(57) ABSTRACT

A process for preparing shaped catalyst bodies whose active composition is a multielement oxide, in which a finely divided precursor mixture with addition of graphite having a specific particle size is shaped to the desired geometry and then treated thermally.

29 Claims, 3 Drawing Sheets

(56) References Cited

U.S. PATENT DOCUMENTS

Figure 1:
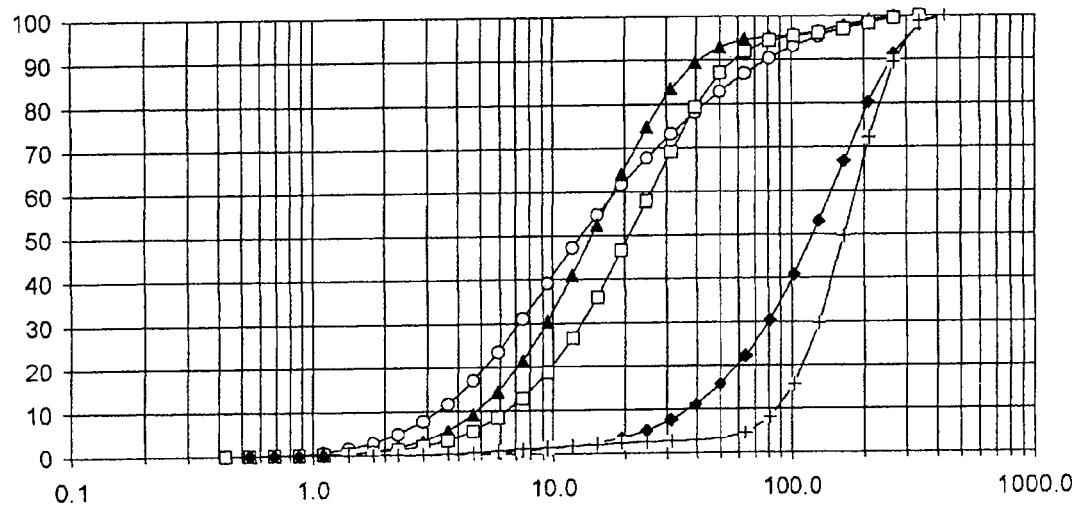

| | | |
|---|---|---|
| 7,060,649 B2 | 6/2006 | Weiguny et al. |
| 7,157,403 B2 | 1/2007 | Weiguny et al. |
| 7,196,217 B2 | 3/2007 | Schliephake et al. |
| 2005/0065371 A1 | 3/2005 | Petzoldt et al. |
| 2005/0131253 A1 | 6/2005 | Teshigahara et al. |
| 2007/0032377 A1 | 2/2007 | Hibst et al. |
| 2008/0227992 A1 | 9/2008 | Dobner et al. |

FOREIGN PATENT DOCUMENTS

| | | |
|---|---|---|
| DE | 10 2005 035 978 A1 | 2/2007 |
| DE | 10 2005 037 678 A1 | 2/2007 |
| EP | 0 467 144 A1 | 1/1992 |
| EP | 1 060 792 A1 | 12/2000 |
| WO | WO 95/07144 | 3/1995 |
| WO | WO 01/68245 A1 | 9/2001 |
| WO | WO 03/078059 A1 | 9/2003 |
| WO | WO 03/078310 A2 | 9/2003 |
| WO | WO 2005/030393 A1 | 4/2005 |

OTHER PUBLICATIONS

U.S. Appl. No. 12/557,021, filed Sep. 10, 2009, Raichle, et al.
U.S. Appl. No. 12/546,883, filed Aug. 25, 2009, Raichle, et al.
U.S. Appl. No. 12/634,149, filed Dec. 9, 2009, Raichle, et al.

* cited by examiner

PROCESS FOR PREPARING SHAPED CATALYST BODIES WHOSE ACTIVE COMPOSITION IS A MULTIELEMENT OXIDE

The present invention relates to a process for preparing shaped catalyst bodies whose active composition is a multielement oxide, in which a finely divided precursor mixture which comprises added graphite as a finely divided shaping assistant is shaped (compacted) to the desired geometry and the resulting shaped catalyst precursor bodies are treated thermally at elevated temperature to obtain the shaped catalyst bodies whose active composition is a multielement oxide.

The present invention further relates to processes for heterogeneously catalyzed gas phase reactions, for example gas phase partial oxidations of organic compounds in which the aforementioned shaped catalyst bodies are used as catalysts. Examples of such heterogeneously catalyzed partial oxidation processes are the preparation of acrolein from propylene (WO 2005/030393), the preparation of methacrylic acid from methacrolein (EP-A 467 144) and the preparation of maleic anhydride from n-butane (WO 01/68245).

Acrolein is, for example, an important intermediate in the preparation of acrylic acid, which is obtainable by heterogeneously catalyzed partial oxidation of acrolein. Acrylic acid is an important monomer which can be free-radically polymerized as such or in the form of its alkyl esters. The resulting polymers are suitable, inter alia, as superabsorbent materials or as adhesives. Methacrylic acid is also suitable correspondingly as such or in the form of its alkyl esters for preparing free-radical polymers. An outstanding position is occupied, for example, by the methyl ester of methacrylic acid, which finds use in particular for the preparation of polymethyl methacrylate which is used as plastic glass.

Maleic anhydride is an important intermediate in the synthesis of γ-butyrolactone, tetrahydrofuran and 1,4-butanediol, which are in turn used as solvents or, for example, processed further to polymers such as polytetrahydrofuran or polyvinylpyrrolidone.

In this document, a complete oxidation of an organic compound with molecular oxygen is understood to mean that the organic compound is converted with the reactive action of molecular oxygen such that all of the carbon present in the organic compound is converted to oxides of carbon and all of the hydrogen present in the organic compound is converted to oxides of hydrogen. All other reactions of an organic compound with the reactive action of molecular oxygen are summarized here as partial oxidations of an organic compound.

In particular, in this document, partial oxidations shall be understood to mean those reactions of organic compounds under the reactive action of molecular oxygen in which the organic compound to be oxidized partially, after the reaction has ended, comprises at least one oxygen atom more in chemically bound form than before performance of the partial oxidation. In this document, the term "partial oxidation" shall also comprise oxidative dehydrogenation and partial ammoxidation, i.e. a partial oxidation in the presence of ammonia.

It is common knowledge that multielement oxides (especially multimetal oxides) are especially suitable active compositions for catalysts for performing heterogeneously catalyzed partial oxidations of organic compounds in the gas phase (cf., for example, all heterogeneously catalyzed partial oxidations detailed in DE-A 103 53 014 and in DE-A 103 60 396).

Processes described at the outset for preparing shaped catalyst bodies are known, for example, from the documents WO 01/68245, WO 2005/030393, DE-A 10 2005 035 978, EP-A 1 060 792, WO 03/078310, WO 03/78059, DE-A 10 2005 037 678, EP-A 467 144 and Research Disclosure RD 2005-497012. The majority of the aforementioned documents do not attach any importance whatsoever to the properties of the graphite used as a shaping assistant with regard to the performance of the resulting shaped catalyst body (especially as a catalyst for heterogeneously catalyzed partial oxidations of organic compounds in the gas phase).

Only in working examples of WO 2005/030393 and in comparative examples of Research Disclosure RD 2005-497012 is it noted, without making any judgment, that the specific surface area of the graphite used is from 6 to 13 $m^2/g$ and its particle diameter $d_{50}$ has a value of 19.3 μm.

In other words, the graphite shaping assistant is added in the shaped catalyst body preparation in aforementioned documents essentially exclusively as a lubricant, i.e. in order to reduce the mechanical wear on the shaping tools.

US-A 2005/0131253 relates to a process for preparing shaped catalyst bodies based on multielement oxides using finely divided graphite as a shaping assistant with a particle diameter $d_{50}$ of from 10 to 50 μm. In the exemplary embodiments, $d_{50}$ is 31 and 29 μm. However, an essential property of the finely divided graphite is considered to be not its particle size but rather its "combustion initiating temperature", which should be at least 50° C. above the calcination temperature employed.

However, a disadvantage of the prior art processes described is that they have not recognized the influence of the properties of the particularity of the finely divided graphite used as a shaping assistant on the catalytic profile (especially on the selectivity of target product formation in partial gas phase oxidations of organic starting compounds heterogeneously catalyzed by them) of the resulting shaped catalyst bodies. Against this background, it was an object of the present invention to provide an improved process for preparing shaped catalyst bodies, which results in particular in shaped catalyst bodies which enable, in particular, improved target product selectivities when they are used as catalysts for heterogeneously catalyzed partial gas phase oxidations of organic starting compounds.

Accordingly, a process has been found for preparing shaped catalyst bodies whose active composition is a multielement oxide, in which a finely divided precursor mixture which comprises added graphite as a finely divided shaping assistant is shaped (compacted) to the desired geometry and the resulting shaped catalyst precursor bodies are treated thermally at elevated temperature to obtain the shaped catalyst bodies whose active composition is a multielement oxide, wherein a) for the specific surface area $O_G$ of the finely divided graphite:

$$0.5\ m^2/g \leq O_G \leq 5\ m^2/g$$

and b) for the particle diameter $d_{50}$ of the finely divided graphite:

$$40\ \mu m \leq d_{50} \leq 200\ \mu m.$$

In other words, the use of graphite with particles of reduced coarseness compared to the prior art and low specific surface area is capable of achieving the object of the invention.

The shaped catalyst bodies may, for example, be a sphere having a diameter of from 2 to 10 mm, or a solid cylinder having an external diameter and a height of from 2 to 10 mm, or a ring whose external diameter and height are from 2 to 10 mm and whose wall thickness is from 1 to 3 mm.

Processes advantageous in accordance with the invention for preparing shaped catalyst bodies are in particular those which use finely divided graphite as a shaping assistant, for which, firstly, 40 µm≤$d_{50}$≤200 µm, and, secondly, 0.5 m$^2$/g≤$O_G$≤4 m$^2$/g, preferably 0.75 m$^2$/g≤$O_G$≤3 m$^2$/g, more preferably 1 m$^2$/g≤$O_G$≤2.5 m$^2$/g and most preferably 1.25 m$^2$/g≤$O_G$≤2.5 m$^2$/g or 1.5 m$^2$/g≤$O_G$≤2 m$^2$/g.

According to the invention, a very particularly advantageous use is that of those finely divided graphites as shaping assistants for which, firstly, 50 µm≤$d_{50}$≤200 µm, and, secondly, 0.5 m$^2$/g≤$O_G$≤5 m$^2$/g, preferably 0.5 m$^2$/g≤$O_G$≤4 m$^2$/g, 0.75 m$^2$/g≤$O_G$≤3 m$^2$/g, more preferably 1 m$^2$/g≤$O_G$≤2.5 m$^2$/g and most preferably 1.25 m$^2$/g≤$O_G$≤2.5 m$^2$/g or 1.5 m$^2$/g≤$O_G$≤2 m$^2$/g.

According to the invention, an even more advantageous use is that of those finely divided graphites as shaping assistants for which, firstly, 60 µm (or 70 µm)≤$d_{50}$≤200 µm, and, secondly, 0.5 m$^2$/g≤$O_G$≤5 m$^2$/g, preferably 0.5 m$^2$/g≤$O_G$≤4 m$^2$/g, 0.75 m$^2$/g≤$O_G$≤3 m$^2$/g, more preferably 1 m$^2$/g≤$O_G$≤2.5 m$^2$/g and most preferably 1.25 m$^2$/g≤$O_G$≤2.5 m$^2$/g or 1.5 m$^2$/g≤$O_G$≤2 m$^2$/g.

However, according to the invention, the most advantageous use is that of those finely divided graphites as shaping assistants for which, firstly, 90 µm (or 100 µm)≤$d_{50}$≤170 µm, and, secondly, 0.5 m$^2$/g≤$O_G$≤5 m$^2$/g, preferably 0.5 m$^2$/g≤$O_G$≤4 m$^2$/g, 0.75 m$^2$/g≤$O_G$≤3 m$^2$/g, more preferably 1 m$^2$/g≤$O_G$≤2.5 m$^2$/g and most preferably 1.25 m$^2$/g≤$O_G$≤2.5 m$^2$/g or 1.5 m$^2$/g≤$O_G$≤2 m$^2$/g.

It is also favorable in accordance with the invention when, within the aforementioned framework, with a $d_{50}$ of ≤90 µm and ≤200 µm, the particle diameters $d_{10}$ and $d_{90}$ of the finely divided graphite simultaneously fulfill the following conditions:

$$20\ \mu m \leq d_{10} \leq 90\ \mu m, \text{ and}$$

$$150\ \mu m \leq d_{90} \leq 300\ \mu m.$$

In general, it will be the case that $d_{10} < d_{50} < d_{90}$.

In principle, for the process according to the invention, it is possible to use either synthetic (synthetically produced) or natural (naturally occurring) graphite. Preference is given in accordance with the invention to the use of natural graphite since it has particularly favorable lubricant properties owing to its marked layer structure. Very particularly advantageous natural graphites in accordance with the invention are those which are essentially free of mineral impurities.

It is also advantageous for the preparation process according to the invention when the thermal treatment of the shaped catalyst bodies until the shaped catalyst bodies are obtained (this treatment forms the catalytically active multielement oxide composition from the precursor composition) converts at least 1% by weight, preferably at least 2% by weight, more preferably at least 3% by weight and most preferably at least 5% by weight of the amount of graphite present in the shaped catalyst precursor bodies (calculated as pure amount of carbon) to compounds which escape in gaseous form (for example combusts them to CO and/or $CO_2$). Appropriately in accordance with the invention, the aforementioned proportion by weight which escapes in gaseous form in the thermal treatment of the shaped catalyst precursor bodies until the shaped catalyst bodies are obtained in the amount of graphite present in the shaped catalyst precursor bodies (calculated as pure amount of carbon) is, however, not more than 70% by weight, preferably not more than 60% by weight, more preferably not more than 50% by weight and most preferably not more than 40% by weight or not more than 30% by weight.

Appropriately from an application point of view, the aforementioned proportion by weight is from 5 to 15% by weight.

Typical amounts of graphite used in the process according to the invention range from 0.1 to 35 or to 20% by weight, or from 0.5 to 10% by weight, or from 1 or 2 to 5% by weight (calculated as pure carbon and based on the mass of the shaped catalyst pre-cursor body). Frequently, the amount of graphite used, on this basis, is from 2 to 5% by weight. When an exceptionally pore-forming action is desired, however, a use amount of graphite of from 15 to 35% by weight may also be advantageous.

Normally, the finely divided precursor mixture which comprises added finely divided graphite as a finely divided shaping assistant (compacting assistant) in accordance with the invention is dry in the course of shaping (dry to the touch).

In general, the finely divided precursor mixture comprises the graphite to be added in accordance with the invention as the sole added shaping assistant. In principle, the inventive addition of graphite to the finely divided precursor mixture can also be effected together with other shaping assistants, for example boron nitride, carbon black, polyethylene glycol, stearic acid, starch, polyacrylic acid, mineral or vegetable oil, water, finely divided Teflon powder (for example powder from Aldrich 43093-5) and/or boron trifluoride.

Advantageously in accordance with the invention, and adjusted to the particular type of multielement oxide (active) composition desired in each case, the thermal treatment of the shaped catalyst precursor bodies can be effected at temperatures (which act externally on the shaped catalyst bodies) of from 150 to 650° C. Frequently, the thermal treatment of the shaped catalyst precursor bodies will be effected at temperatures in the range from 200° C. to 600° C., or from 250° C. to 550° C., or from 300° C. to 500° C. The duration of the thermal treatment may extend over a period of from a few hours up to several days. The thermal treatment can be effected under reduced pressure, under inert atmosphere (e.g. $N_2$, noble gases, steam, $CO_2$, etc.), under reducing atmosphere (e.g. $H_2$ or $NH_3$) or under oxidizing atmosphere. In general, oxidizing atmospheres will comprise molecular oxygen. Typical oxidizing atmospheres are mixtures of inert gas ($N_2$, noble gases, steam, $CO_2$, etc.) and molecular oxygen. Typically, the content of molecular oxygen will be at least 0.1% by volume, frequently at least 0.2% by volume, in many cases at least 0.5% by volume, often at least 1% by volume, or at least 10% by volume, or at least 20% by volume. It will be appreciated that the content of molecular oxygen in such mixtures may also be 30% by volume, or 40% by volume, or 50% by volume, or 70% by volume, or more.

It will be appreciated that a useful atmosphere for the thermal treatment is also pure molecular oxygen. Frequently, the thermal treatment will be effected under air. Generally, the thermal treatment of the shaped catalyst precursor bodies can be effected under a standing or a flowing gas atmosphere (for example in an air stream).

The term "atmosphere" (or "gas atmosphere") in which the thermal treatment is effected should be understood in this document such that it does not comprise gases which evolve from the shaped catalyst precursor bodies in the course of the thermal treatment owing to decomposition procedures. It will be appreciated that the gas atmosphere in which the thermal treatment is effected may also consist exclusively or partly of these gases. In the course of the thermal treatment which is effected in the process according to the invention, both the treatment temperature and the treatment atmosphere may be constant or variable over the treatment time.

Since graphite, as a carbon-comprising substance, is combustible, the thermal treatment of the shaped catalyst precursor bodies comprising added finely divided graphite is effected in accordance with the invention in a manner known per se appropriately from an application point of view normally such that the graphite present in the shaped catalyst precursor bodies does not ignite during the thermal treatment, in order thus to very substantially prevent any temperatures in the shaped body interior which go well above the temperature which acts on the shaped catalyst precursor bodies from outside in the course of the thermal treatment (so-called hotspot temperatures in the calcination material), since such temperature peaks can reduce the catalytic quality of the resulting shaped catalyst bodies. This aim requires a certain degree of care especially when the atmosphere in which the thermal treatment is effected comprises molecular oxygen as such and/or constituents which afford molecular oxygen and/or a graphite-oxidizing action results from the composition of the precursor mass itself. In this context, it should be taken into account that naturally occurring graphite is generally a mixture of graphite and mineral constituents which are capable of catalyzing ignition of the graphite. The particularity and the surface properties of the graphite used in accordance with the invention also influence its ignition behavior.

In this connection, it is generally advantageous for the process according to the invention when that temperature $T_i$ (the sample temperature or, more specifically, the oven temperature) at which a weight loss in the graphite to be used in accordance with the invention is observed for the first time in simultaneous dynamic differential calorimetry-thermogravimetry (in this document, $T_i$ shall be referred to as the "temperature of initial combustion") is at least 50° C., better at least 75° C., even better at least 100° C., preferably at least 125° C. and more preferably at least 150° C. greater than the highest temperature which acts thereon for a period of at least 30 minutes in the course of the inventive thermal treatment of the shaped catalyst precursor bodies.

Since the result of a determination of $T_i$ by means of a simultaneous dynamic differential calorimetry-thermogravimetry is not only a function of the graphite to be examined by this method but also a pronounced function of the selected testing conditions (for example also the amount of sample analyzed), the temperature $T_i$ used in this document is based on the testing principle described below, including the testing conditions specified:

The graphite sample to be tested (analyzed) (sample amount=10 mg) is subjected in an open sample crucible ($Al_2O_3$) in a test unit having a vertical tube oven (Netzsch STA 449 C Jupiter®; instrument type: simultaneous thermoanalysis, coupling of dynamic heat flow differential calorimeter and compensating thermal balance with vertical tube oven) from NETZSCH-Gerätebau GmbH, Wittelsbacherstraße 42, 95100 Selb, Bavaria to a predefined temperature program (heating rate=0.3 K/min; temperature range=30° C. (start temperature) to 1000° C. (end temperature)). The oven atmosphere used is air with a flow rate of 20.0 $cm^3$/min.

According to the oven temperature, the temperature difference between the graphite sample to be tested and an empty inert reference sample crucible ($Al_2O_3$) in defined thermal contact to the sample is used to determine the heat flux from and to the sample. Sample crucible with sample, reference sample crucible without sample and the thermal sensor are on a balance. This makes possible thermogravimetry (TG) (=method for measuring the change in mass (or change in weight) of a sample in the course of the temperature program; the sample mass is measured as a function of the oven temperature) simultaneously with the dynamic differential calorimetry (DSC=dynamic scanning calorimetry; method for quantifying calorific effects).

The TG resolution is 0.1 µg and the DSC resolution is <1 µW.

Apart from these, the testing is effected in accordance with DIN 51006 and DIN 51007. $T_i$ values of graphite to be used in accordance with the invention of ≥500° C., preferably ≥550° C., are found to be advantageous in many preparation processes according to the invention. In general, $T_i$ is, however, at values of ≤700° C., usually ≤650° C.

For the process according to the invention, it is also favorable when, in the above-described thermogravimetry of the graphite to be used in accordance with the invention, that temperature $T_m$ (sample temperature or, better, oven temperature) at which the decrease in the mass of the graphite sample with the increase in temperature attains its maximum value (referred to in this document as "temperature of the combustion maximum") is at a maximum. Advantageously, $T_m$ for graphites to be used in accordance with the invention is ≥680° C., preferably ≥700° C. and more preferably ≥750° C. In general, $T_m$ is at values of ≤900° C., in many cases at values of ≤850° C.

In addition, it is favorable for the process according to the invention when, in the above-described thermogravimetry of the inventive graphite, that temperature $T_f$ (sample temperature or, better, oven temperature) from which no further weight loss is observed (at which the weight loss has ended) is from 150 to 350° C. (appropriately 250° C.) above $T_i$.

At this point, it should be emphasized that all data in this document for specific surface areas of graphites are based on determinations to DIN 66131 (determinations of the specific surface area of solids by gas adsorption ($N_2$) according to Brunauer-Emmet-Teller (BET)).

All data in this document for total pore volumes and for pore diameter distributions over these total pore volumes and for specific surface areas (in each case of the shaped catalyst bodies) are based on determinations by the method of mercury porosimetry using the Auto Pore 9220 from Micromeritics GmbH, 4040 Neuss, Germany (bandwidth from 30 Å to 0.3 mm). Otherwise, the determination method is specified.

To determine the particle diameter distributions and the particle diameters $d_{10}$, $d_{50}$ and $d_{90}$ derived from these, the particular finely divided powder was conducted through a dispersing channel in the dry disperser Sympatec RODOS (Sympatec GmbH, System-Partikel-Technik, Am Pulverhaus 1, D-38678 Clausthal-Zellerfeld) and dry-dispersed there with compressed air and blown into the measurement cell in a free jet. The volume-based particle diameter distribution is then determined therein to ISO 13320 with a Mastersizer S laser diffraction spectrometer (Malvern Instruments, Worcestershire WR14 1AT, United Kingdom). The particle diameters $d_x$ reported as the measurement result are defined such that X % of the total particle volume consists of particles with this diameter or a smaller diameter.

To determine the graphite content (calculated as pure amount of carbon) in the shaped catalyst precursor body and in the finished shaped catalyst body, it is possible, for example, to comminute a representative sample of the particular shaped bodies to a powder. In that case, the determination is effected on an identical proportion in each case, which, in absolute terms, appropriately has a mass of from 50 to 20 mg. This pulverulent sample is then introduced in countercurrent with an oxygen stream into a horizontal quartz tube heated to about 1000° C. and calcined. The resulting combustion gas is passed through an IR cell and the amount of carbon dioxide present therein is determined quantitatively by infrared absorption. The particular graphite content (calculated as pure amount of carbon) can be calculated from the amount of carbon dioxide detected (cf. "Quantitative Organische Elementaranalyse" [Quantitative organic elemental analysis], VCN Verlagsgesellschaft mbH, Weinheim; 1991 Edition; ISBN: 3-527-28056-1, page 225 ff).

The particle diameters of the finely divided precursor mixture (excluding the added shaping assistant) will (for at least 90% of the weight of the precursor mixture) generally be in the range from 10 to 2000 μm when it is shaped to the desired geometry of the shaped catalyst precursor body. In many cases, aforementioned particle diameters will be in the range from 20 to 1800 μm, or from 30 to 1700 μm, or from 40 to 1600 μm, or from 50 to 1500 μm. Particularly frequently, these particle diameters will be from 100 to 1500 μm, or from 150 to 1500 μm.

In general, the finely divided precursor mixture is shaped (compacted) to the geometry of the shaped catalyst precursor body by the action of external forces (pressure) on the finely divided precursor mixture. The shaping apparatus to be employed and the shaping method to be employed are not subject to any restriction. Equally, the desired geometry of the shaped catalyst precursor body is not subject to any restriction. In other words, the shaped catalyst precursor bodies may have a regular or irregular shape, preference generally being given to regularly shaped bodies.

The catalyst precursor body may have spherical geometry. In this case, the sphere diameter may, for example, be from 2 to 10 mm, or from 4 to 8 mm. The geometry of the shaped catalyst precursor body may also be a solid cylinder or a hollow cylinder.

In both cases, external diameter and height may, for example, be from 2 to 10 mm or from 2 or 4 to 8 mm. In the case of hollow cylinders, a wall thickness of from 1 to 3 mm is generally appropriate. It will be appreciated that useful catalyst precursor geometries are also all of those which are disclosed and recommended in WO 02/062737. In general, the geometry of the resulting shaped catalyst body in the process according to the invention deviates only insignificantly from the geometry of the shaped catalyst precursor body.

At this point, it should be emphasized that processes which are particularly advantageous in accordance with the invention for preparing shaped catalyst bodies and hence particularly favorable shaped catalyst bodies result when graphite to be used in accordance with the invention is used in the places where finely divided graphite is used in the preparation processes disclosed in the documents Research Disclosure RD 2005-497012, EP-A 1 060 792, DE-A 10 2005 035 978, DE-A 10 2005 037 678, WO 03/78059, WO 03/78310, DE-A 198 55 913, WO 02/24620, DE-A 199 22 113, WO 01/68245, EP-A 467 114, US-A 2005/0131253, WO 02/062737 and WO 05/030393, and all other preparation measures are retained unchanged. The resulting shaped catalyst bodies can then be used in an entirely corresponding manner for the corresponding heterogeneously catalyzed gas phase reactions as described in the documents DE-A 199 22 113, WO 01/68245, EP-A 467 114, DE-A 198 55 913, US-A 2005/0131253, WO 02/24620, WO 03/78059, WO 03/078310, WO 02/062737, Research Disclosure RD 2005-497012, EP-A 1 060 792, DE-A 10 2005 035 978, DE-A 10 2005 037 678, and WO 05/030393. They are especially advantageous when the graphite used is the natural graphite Asbury 3160 and/or the synthetic graphite Asbury 4012 from Asbury Graphite Mills, Inc., New Jersey 08802, USA. Especially when synthetic graphites are used, it is generally beneficial for the lubricant properties to employ increased use amounts of the graphite to be used. Generally, but in particular in the case of use amounts of graphite of ≥3% by weight, it may be advantageous to prevent excessively rapid decomposition (which can lead, for example, to crack formation or to a reduction in the catalyst quality) by prolonging one or more hold times in the temperature range between $T_i$ and $T_m$, by adding additional heating ramps or heating zones, and/or by adjusting temperatures.

The shaping can be effected in the process according to the invention, for example, by tableting or extruding. As already mentioned, the finely divided precursor mixture is typically used dry to the touch. However, it may comprise added substances which are liquid under standard conditions (25%, 1 atm) in up to 10% of its total weight. However, the process according to the invention can also be employed when the finely divided precursor mixture no longer comprises any such liquid substances at all. It will be appreciated that the finely divided precursor mixture may also consist of solid solvates (for example hydrates) which have such liquid substances in chemically and/or physically bound form.

The shaping pressures employed in the process according to the invention will generally be from 50 kg/cm$^2$ to 5000 kg/cm$^2$. The shaping pressures are preferably from 200 to 3500 kg/cm$^2$, more preferably from 600 to 2500 kg/cm$^2$. The aforementioned is especially true when the shaping process employed is tableting. The basic features of tableting are described, for example, in "Die Tablette", Handbuch der Entwicklung, Herstellung und Qualitatssicherung ["The Tablet", Handbook of Development, Production and Quality Assurance], W. A. Ritschel and A. Bauer-Brandl, 2nd Edition, Editio Cantor Verlag Aulendorf, 2002, and are applicable in an entirely corresponding manner to an inventive tableting process.

Useful multielement oxide compositions in the process according to the invention are both active compositions which, in addition to oxygen, comprise both metals and non-metals as elemental constituents. The multielement oxide active compositions are, though, frequently pure multimetal oxide (active) compositions.

Multielement oxide (active) compositions particularly favorable for employment of the process according to the invention, including accompanying precursor compositions, are, for example, those which are disclosed in the documents WO 2005/030393, EP-A 467 144, EP-A 1 060 792, DE-A 198 55 913, WO 01/68245, EP-A 1060792, Research Disclosure RD 2005-497012, WO 03/078310, DE-A 102005035978, DE-A 102005037678, WO 03/78059, WO 03/078310, DE-A 199 22 113, WO 02/24620, WO 02/062737 and US-A 2005/0131253.

Finely divided precursor mixtures useable in accordance with the invention are obtainable in the simplest manner, for example by generating, from sources of the elemental constituents of the desired active composition (multielement oxide composition), a finely divided, very intimate shapeable mixture having a composition corresponding to the stoichiometry of the desired active composition, to which shaping assistants and, if desired, reinforcing assistants may be added (and/or may be incorporated from the outset).

Useful sources of the elemental constituents of the desired active composition are in principle those compounds which are already oxides and/or those compounds which can be converted to oxides by heating, at least in the presence of gaseous molecular oxygen and/or of components which release gaseous molecular oxygen. In principle, the oxygen source may also be part of the precursor mixture, for example, in the form of a peroxide. The precursor mixture may also comprise added compounds such as NH$_4$OH, (NH$_4$)$_2$CO$_3$, NH$_4$NO$_3$, NH$_4$CHO$_2$, CH$_3$COOH, NH$_4$CH$_3$CO$_2$, ammonium oxalate and/or organic components such as stearic acid, which dissociate and/or can be decomposed in the thermal treatment as pore formers to give compounds which escape entirely in gaseous form.

The starting compounds (sources) can be mixed, preferably intimately, to prepare the finely divided shapeable precursor mixture in the process according to the invention in dry or in wet form. When it is done in dry form, the starting compounds are appropriately used in the form of finely divided powder (having a particle diameter $d_{50}$ appropriate in the range from 1 to 200 µm, preferably from 2 to 180 µm, more preferably from 3 to 170 µm and most preferably from 4 to 160 µm, or from 5 to 150 µm or from 10 to 120 µm, or from 15 to 80 µm). Addition of the inventive shaping assistants and, if appropriate, addition of further shaping and/or reinforcing assistants may be followed by the shaping. Such reinforcing assistants may, for example, be microfibers of glass, asbestos, silicon carbide and/or potassium titanate. Quite generally, one starting compound may be the source of more than one elemental constituent in the process according to the invention.

Instead of shaping the finely divided precursor mixture as such immediately to the desired geometry, it is frequently appropriate, as a first shaping step, first to carry out an intermediate compaction thereof in order to coarsen the powder (generally to particle diameters of from 100 to 2000 µm, preferably from 150 to 1500 µm, more preferably from 400 to 1250 µm, or from 400 to 1000 µm, or from 400 to 800 µm).

Even before the intermediate compaction, it is possible to add graphite to be used in accordance with the invention as a compacting assistant. Subsequently, the final (actual) shaping is effected on the basis of the coarsened powder, for which it is possible if required again to add finely divided inventive graphite (and, if appropriate, further shaping and/or reinforcing assistants) beforehand.

However, preference is given in accordance with the invention to effecting the intimate mixing in wet form. Typically, the starting compounds are mixed with one another, for example, in the form of an aqueous solution and/or suspension (but liquids such as isobutanol are also useful as a solution and/or dispersion medium). Particularly intimate shapeable mixtures are obtained when the starting materials are exclusively sources of the elemental constituents present in dissolved form. The solvent used is preferably water (but liquids such as isobutanol are also useful as solvents). Subsequently, the resulting solution or suspension is dried, the drying operation preferably being effected by spray-drying with exit temperatures of from 100 to 150° C. (in some cases, the drying can also be effected by filtration and subsequent drying of the filtercake). The particle diameter $d_{50}$ of the resulting spray powder is typically from 10 to 50 µm. When water has been the basis of the liquid medium, the resulting spray powder will normally not comprise more than 20% of its weight, preferably not more than 15% of its weight and more preferably not more than 10% of its weight of water. These percentages generally also apply when other liquid solvents or suspension assistants are employed. After addition of the inventive shaping assistants and, if appropriate, further shaping and/or reinforcing assistants to the particular dry mass which has been made pulverulent, the pulverulent mixture, as a finely divided precursor mixture, may be compacted (shaped) in accordance with the invention to give the desired shaped catalyst precursor body. The finely divided shaping and/or reinforcing assistants may also already have been added to the spray slurry beforehand (partly or fully).

An only partial removal of the solvent or suspension medium may also be appropriate when its additional use as a shaping assistant is intended. Before the inventive addition of the finely divided graphite, it is also possible for a first thermal treatment of the dry powder to be effected. In that case, addition of the graphite is followed by the shaping and the inventive further thermal treatment.

Instead of shaping the finely divided precursor mixture based on the spray powder as such immediately to the desired geometry, it is frequently appropriate, as a first shaping step, first to carry out an intermediate compaction in order to coarsen the powder (generally to particle diameters of from 100 to 2000 µm, preferably from 150 to 1500 µm, more preferably from 400 to 1250 µm, or from 400 to 1000 µm, or from 400 to 800 µm).

Even before the intermediate compaction, it is possible to add graphite to be used in accordance with the invention as a compacting assistant. Subsequently, the final (actual) shaping is effected on the basis of the coarsened powder, for which it is possible if required again to add finely divided inventive graphite (and, if appropriate, further shaping and/or reinforcing assistants) beforehand.

It will be appreciated that the sources used of the elemental constituents may also be starting compounds which have themselves been obtained by thermal treatment of shaped precursor bodies, and are of multielement oxide nature. In particular, the starting compounds of the elemental constituents may be of multimetallic nature.

The process according to the invention is suitable especially for preparing shaped catalyst bodies whose active composition is a multielement oxide, within which the element Mo (or the elements V and P) is the numerically (calculated in molar terms) most frequently occurring element. In particular, it is suitable for preparing shaped catalyst bodies whose active composition is a multielement oxide which comprises the elements Mo, Fe and Bi, or the elements Mo and V, or the elements Mo, V and P, or the elements V and P. The first shaped catalyst bodies in the above list are suitable in particular for heterogeneously catalyzed partial gas phase oxidations of propylene to acrolein. The second shaped catalyst bodies are suitable in particular for heterogeneously catalyzed partial gas phase oxidations of acrolein to acrylic acid, the shaped catalyst bodies mentioned second to last in the above list are suitable in particular for heterogeneously catalyzed partial gas phase oxidations of methacrolein to methacrylic acid, and the shaped catalyst bodies mentioned last are suitable in particular for heterogeneously catalyzed partial gas phase oxidations of n-butane to maleic anhydride.

In particular, the present invention comprises a process for preparing annular shaped catalyst bodies (also known as unsupported catalysts because they do not have any inert support body to which the active composition has been applied) with curved and/or uncurved top surface of the rings, whose active composition (graphite remaining in the active composition is disregarded as always in this document, since it normally behaves chemically inertly and is not catalytically active) has a stoichiometry of the general formula I $$Mo_{12}Bi_aFe_bX^1_cX^2_dX^3_eX^4_fO_n \qquad (I),$$

where
$X^1$=nickel and/or cobalt,
$X^2$=thallium, an alkali metal and/or an alkaline earth metal,
$X^3$=zinc, phosphorus, arsenic, boron, antimony, tin, cerium, lead, vanadium, chromium and/or tungsten,
$X^4$=silicon, aluminum, titanium and/or zirconium,
a=0.2 to 5,
b=0.01 to 5,
c=0 to 10,
d=0 to 2,
e=0 to 8,
f=0 to 10 and
n=a number which is determined by the valency and frequency of the elements in I other than oxygen, or a stoichiometry of the general formula II $$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \qquad (II)$$

where
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum or tungsten, or molybdenum and tungsten,
a'=0.01 to 8,
b'=0.1 to 30,
c'=0 to 4,
d'=0 to 20,
e'>0 to 20,
f'=0 to 6,
g'=0 to 15,
h'=8 to 16,
x', y'=numbers which are determined by the valency and frequency of the elements in II other than oxygen and
p, q=numbers whose p/q ratio is from 0.1 to 10,
and whose annular geometry, without taking into account any existing curvature of the top surface, has a height H of from 1.5 to 8 mm, an external diameter E of from 2 to 11 mm and a wall thickness W of from 0.75 mm to 2.0 mm.

In this process, a finely divided shapeable precursor mixture will be obtained from sources of the elemental constituents of the active composition and annular shaped unsupported catalyst precursor bodies whose top surfaces are curved and/or uncurved will be formed from this mixture after addition of inventive shaping assistant and, if appropriate, further shaping and/or reinforcing assistant, and these shaped bodies will be converted to the annular unsupported catalysts by thermal treatment at elevated temperature.

The present invention also relates to the use of the above annular unsupported catalysts obtainable in accordance with the invention as catalysts with increased selectivity (at comparable activity) for the catalytic partial oxidation of propene to acrolein in the gas phase, and also of isobutene or tert-butanol or its methyl ether to methacrolein.

The aforementioned process for preparing annular shaped catalyst bodies is particularly advantageous when the finely divided precursor mixture is shaped (compacted) in such a way that the side crushing strength of the resulting annular shaped unsupported catalyst precursor bodies is ≥10 and ≤40 N, better ≥10 and ≤35 N, even better ≥12 and ≤23 N. The side crushing strength of the resulting annular shaped unsupported catalyst precursor bodies is preferably ≥13 N and ≤22 N, or ≥14 N and ≤21 N. Most preferably, the side crushing strength of the resulting annular shaped unsupported catalyst precursor bodies is ≥16 N and ≤21 N.

Moreover, for these catalyst types, the particle size (the particle diameter) of the finely divided precursor mixture (excluding the assistants to be added) is advantageously from 200 μm to 1500 μm, more advantageously from 400 μm to 1000 μm (for example, established by intermediate compaction). Favorably, at least 80% by weight, better at least 90% by weight and more advantageously at least 95 or 98 or more % by weight of the finely divided precursor mixture is within this particle size range. In this document, side crushing strength is understood to mean the crushing strength when the annular shaped unsupported catalyst precursor body is compressed at right angles to the cylindrical shell (i.e. parallel to the surface of the ring orifice). All side crushing strengths in this document relate to a determination by means of a Z 2.5/TS15 material testing machine from Zwick GmbH & Co (D-89079 Ulm). This material testing machine is designed for quasistatic stress having a single-impetus, stationary, dynamic or varying profile. It is suitable for tensile, compressive and bending tests. The installed KAF-TC force transducer from A.S.T. (D-01307 Dresden) with the manufacturer number 03-2038 was calibrated in accordance with DIN EN ISO 7500-1 and was usable for the 1-500 N measurement range (relative measurement uncertainty: ±0.2%).

The measurements were carried out with the following parameters:
Initial force: 0.5 N.
Rate of initial force: 10 mm/min.
Testing rate: 1.6 mm/min.

The upper die was initially lowered slowly down to just above the surface of the cylindrical shell of the annular shaped unsupported catalyst precursor body. The upper die was then stopped, in order subsequently to be lowered at the distinctly slower testing rate with the minimum initial force required for further lowering.

The initial force at which the shaped unsupported catalyst precursor body exhibits crack formation is the side crushing strength (SCS).

Unsupported catalyst ring geometries which are particularly advantageous in accordance with the invention additionally fulfill the condition H/E=from 0.3 to 0.7. Particular preference is given to H/E being from 0.4 to 0.6.

It is also advantageous for the relevant unsupported catalyst rings when the I/E ratio (where I is the internal diameter of the unsupported catalyst ring geometry) is from 0.3 to 0.8, preferably from 0.4 to 0.7.

Particularly advantageous unsupported catalyst ring geometries are those which simultaneously have one of the advantageous H/E ratios and one of the advantageous I/E ratios. Such possible combinations are, for example, H/E=from 0.3 to 0.7 and I/E=from 0.3 to 0.8 or from 0.4 to 0.7. Alternatively, H/E may be from 0.4 to 0.6 and I/E simultaneously from 0.3 to 0.8 or from 0.4 to 0.7.

It is also preferred for the relevant unsupported catalyst rings when H is from 2 to 6 mm and more preferred when H is from 2 to 4 mm.

It is also advantageous when E is from 4 to 8 mm, preferably from 5 to 7 mm.

The wall thickness of the relevant unsupported catalyst ring geometries obtainable in accordance with the invention is advantageously from 1 to 1.5 mm.

In other words, favorable said unsupported catalyst ring geometries are, for example, those where H=from 2 to 6 mm and E=from 4 to 8 mm or from 5 to 7 mm. Alternatively, H may be from 2 to 4 mm and E simultaneously from 4 to 8 mm or from 5 to 7 mm. In all the aforementioned cases, the wall thickness W may be from 0.75 to 2.0 mm or from 1 to 1.5 mm.

Among the aforementioned favorable unsupported catalyst geometries, particular preference is given to those for which the aforementioned H/E and I/E combinations are simultaneously fulfilled.

Possible relevant unsupported catalyst ring geometries are thus (E×H×I) 5 mm×2 mm×2 mm, or 5 mm×3 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm, or 7 mm×7 mm×3 mm, or 7 mm×7 mm×4 mm.

The top surfaces of the rings obtained as described may also either both be, or only one may be, curved as described in EP-A 184 790, and, for example, in such a way that the radius of the curvature is preferably from 0.4 to 5 times the external diameter E. Preference is given in accordance with the invention to both top surfaces being uncurved.

All of these unsupported catalyst ring geometries are suitable, for example, both for catalytic partial oxidation in the gas phase of propene to acrolein and for the catalytic partial oxidation in the gas phase of isobutene or tert-butanol or the methyl ether of tert-butanol to methacrolein.

Regarding the active compositions of the stoichiometry of the general formula I, the stoichiometric coefficient b is preferably from 2 to 4, the stoichiometric coefficient c is preferably from 3 to 10, the stoichiometric coefficient d is preferably from 0.02 to 2, the stoichiometric coefficient e is preferably from 0 to 5 and the stoichiometric coefficient a is preferably from 0.4 to 2. The stoichiometric coefficient f is advantageously from 0.5 or 1 to 10. Particular preference is given to the aforementioned stoichiometric coefficients simultaneously being within the preferred ranges mentioned.

In addition, $X^1$ is preferably cobalt, $X^2$ is preferably K, Cs and/or Sr, more preferably K, $X^3$ is preferably tungsten, zinc and/or phosphorus, and $X^4$ is preferably Si. Particular preference is given to the variables $X^1$ to $X^4$ simultaneously having the aforementioned definitions.

Particular preference is given to all stoichiometric coefficients a to f and all variables $X^1$ to $X^4$ simultaneously having their aforementioned advantageous definitions.

Within the stoichiometries of the general formula II, preference is given to those which correspond to the general formula III

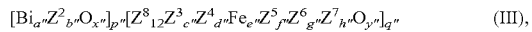

(III), where $Z^2$=molybdenum or tungsten, or molybdenum and tungsten,
$Z^3$=nickel and/or cobalt,
$Z^4$=thallium, an alkali metal and/or an alkaline earth metal, preferably K, Cs and/or Sr,
$Z^5$=phosphorus, arsenic, boron, antimony, tin, cerium, vanadium, chromium and/or Bi,
$Z^6$=silicon, aluminum, titanium and/or zirconium, preferably Si,
$Z^7$=copper, silver and/or gold,
$Z^8$=molybdenum or tungsten, or tungsten and molybdenum,
a"=0.1 to 1,
b"=0.2 to 2,
c"=3 to 10,
d"=0.02 to 2,
e=0.01 to 5, preferably 0.1 to 3,
f"=0 to 5,
g"=0 to 10, preferably >0 to 10, more preferably 0.2 to 10 and most preferably 0.4 to 3,
h"=0 to 1,
x", y"=numbers which are determined by the valency and frequency of the elements in III other than oxygen and
p", q"=numbers whose p"/q" ratio is from 0.1 to 5, preferably from 0.5 to 2.

In addition, preference is given to active compositions of the stoichiometry II which comprise three-dimensional regions of the chemical composition $Y^1{}_a Y^2{}_b O_{x'}$, which are delimited from their local environment as a consequence of their different composition from their local environment and whose longest diameter (longest line passing through the center of the region and connecting two points on the surface (interface) of the region) is from 1 nm to 100 μm, frequently from 10 nm to 500 nm or from 1 μm to 50 or 25 μm.

Particularly advantageous active compositions of the stoichiometry II are those in which $Y^1$ is only bismuth.

Within the active compositions of the stoichiometry III, preference is given in accordance with the invention to those in which $Z^2{}_{b"}$=(tungsten)$_{b"}$ and $Z^8{}_{12}$=(molybdenum)$_{12}$.

In addition, for the annular unsupported catalysts discussed, preference is given to active compositions of the stoichiometry III which comprise three-dimensional regions of the chemical composition $Bi_{a"}Z^2{}_{b"}O_{x"}$ which are delimited from their local environment as a consequence of their different composition than their local environment and whose longest diameter (longest line passing through the center of the region and connecting two points on the surface (interface) of the region) is from 1 nm to 100 μm, frequently from 10 nm to 500 nm or from 1 μm to 50 or 25 μm.

In addition, it is advantageous when at least 25 mol %, (preferably at least 50 mol % and more preferably at least 100 mol %) of the total $[Y^1{}_a Y^2{}_b O_x]_p$ ($[Bi_{a"}Z^2{}_{b"}O_{x"}]_{p"}$) fraction of the active compositions of the stoichiometry II (active compositions of the stoichiometry III) obtainable as described in the active compositions of the stoichiometry II (active compositions of the stoichiometry III) is in the form of three-dimensional regions of the chemical composition $Y^1{}_a Y^2{}_b O_{x'}$ ($[Bi_{a"}Z^2{}_{b"}O_{x"}]$) which are delimited from their local environment as a consequence of their different chemical composition than their local environment and whose longest diameter is in the range from 1 nm to 100 μm.

Useful shaping assistants (lubricants) for the process according to the invention for preparing the relevant annular shaped catalyst bodies, in addition to inventive graphite, are carbon black, polyethylene glycol, stearic acid, starch, polyacrylic acid, mineral or vegetable oil, water, boron trifluoride and/or boron nitride. Glycerol and cellulose ether may also be used as further lubricants. Preference is given in accordance with the invention to adding exclusively graphite to be used in accordance with the invention as a shaping assistant. Based on the composition to be shaped to the shaped unsupported catalyst precursor body, generally ≤15% by weight, usually ≤9% by weight, in many cases ≤5% by weight, often ≤4% by weight of graphite to be used in accordance with the invention is added. Typically, the aforementioned added amount is ≥0.5% by weight, usually ≥2.5% by weight. Inventive graphites which are added with preference are Asbury 3160 and Asbury 4012.

It is also possible to add finely divided reinforcing agents such as microfibers of glass, asbestos, silicon carbide or potassium titanate. The shaping to the annular shaped unsupported catalyst precursor body may be carried out, for example, by means of a tableting machine, an extrusion reshaping machine or the like.

The relevant annular shaped unsupported catalyst precursor body is treated thermally generally at temperatures which exceed 350° C. Normally, the temperature in the course of the thermal treatment will not exceed 650° C. Advantageously in accordance with the invention, the temperature in the course of the thermal treatment will not exceed 600° C., preferably 550° C. and more preferably 500° C. In addition, the temperature in the course of the thermal treatment of the annular shaped unsupported catalyst precursor body will preferably exceed 380° C., advantageously 400° C., particularly advantageously 420° C. and most preferably 440° C. The thermal treatment may also be subdivided into a plurality of sections within its duration. For example, a thermal treatment may initially be carried out at a temperature of from 150 to 350° C., preferably from 220 to 290° C., and be followed by a thermal treatment at a temperature of from 400 to 600° C., preferably from 430 to 550° C.

Normally, the thermal treatment of the annular shaped unsupported catalyst precursor body takes several hours (usually more than 5 h). Frequently, the overall duration of the thermal treatment extends for more than 10 h. Usually, treatment durations of 45 h or 25 h are not exceeded in the course of the thermal treatment of the annular shaped unsupported catalyst precursor body. Often, the overall treatment time is below 20 h. Advantageously in accordance with the invention, 500° C. (460° C.) are not exceeded in the course of the thermal treatment of the relevant annular shaped unsupported catalyst precursor body, and the treatment time within the temperature window of ≥400° C. (≥440° C.) extends to from 5 to 20 h.

The thermal treatment (and also the decomposition phase addressed hereinbelow) of the annular shaped unsupported catalyst precursor bodies may be effected either under inert gas or under an oxidative atmosphere, for example air (mixture of inert gas and oxygen) or else under a reducing atmosphere (for example mixture of inert gas, $NH_3$, CO and/or $H_2$ or methane, acrolein, methacrolein). It will be appreciated that the thermal treatment may also be performed under reduced pressure.

In principle, the thermal treatment of the relevant annular shaped unsupported catalyst precursor bodies may be carried out in highly differing furnace types, for example heatable forced-air chambers, tray furnaces, rotary tube furnaces, belt calciners or shaft furnaces. Preference is given to effecting the thermal treatment of the annular shaped unsupported catalyst precursor bodies in a belt calcining apparatus as recommended by DE-A 100 46 957 and WO 02/24620.

The thermal treatment of the relevant annular shaped unsupported catalyst precursor bodies below 350° C. generally pursues the aim of the thermal decomposition of the sources of the elemental constituents of the desired annular unsupported catalyst present in the shaped unsupported catalyst precursor bodies. Frequently, this decomposition phase proceeds in the course of the heating at temperatures of ≥350° C.

The annular shaped unsupported catalyst precursor bodies of desired annular unsupported catalysts, whose active composition has a stoichiometry of the general formula I, or the general formula II, or the general formula III, may be prepared by generating, from sources of the elemental constituents of the active composition of the desired annular unsupported catalyst, a (very intimate) finely divided shapeable mixture having a composition corresponding to the stoichiometry of the desired active composition and, optionally after adding shaping and, if appropriate, reinforcing assistants (including those in accordance with the invention), forming from this an annular unsupported shaped catalyst precursor body (having curved and/or uncurved top surfaces) whose side crushing strength is ≥12 N and ≤23 N. The geometry of the annular shaped unsupported catalyst precursor body will correspond substantially to that of the desired annular unsupported catalyst.

Useful sources for the elemental constituents of the desired active composition are those compounds which are already oxides and/or those compounds which can be converted to oxides by heating, at least in the presence of molecular oxygen.

In addition to the oxides, useful such starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$, ammonium oxalate and/or organic components, for example stearic acid, which decompose and/or may be decomposed in the course of thermal treatment to give compounds which escape fully in gaseous form may additionally be incorporated into the finely divided shapeable mixture (preferably a dry mixture)).

The preferably intimate mixing of the starting compounds (sources) to prepare the finely divided shapeable mixture in the process according to the invention may be effected in dry or in wet form. When it is effected in dry form, the starting compounds are appropriately used as a finely divided powder (the particle diameter $d_{50}$ should advantageously be ≤100 µm, preferably ≤50 µm; in general the particle diameter $d_{50}$ will be ≥1 µm). After addition of shaping and, if appropriate, reinforcing assistants (including those in accordance with the invention), the shaping to the annular shaped unsupported catalyst precursor body may subsequently be effected.

However, preference is given to effecting the intimate mixing in wet form. Typically, the starting compounds are mixed together in the form of an aqueous solution and/or suspension. Particularly intimate shapeable mixtures are obtained when the starting materials are exclusively sources of the elemental constituents present in dissolved form. The solvent used is preferably water. Subsequently, the resulting solution or suspension is dried, and the drying process is preferably effected by spray-drying with exit temperatures of from 100 to 150° C. The particle diameter $d_{50}$ of the resulting spray powder is typically from 10 to 50 µm, preferably from 15 to 40 µm.

The spray powder may then be compressed (shaped) after addition of shaping and, if appropriate, reinforcing assistants (including those in accordance with the invention) to give the annular shaped unsupported catalyst precursor bodies. However, the finely divided shaping and, if appropriate, reinforcing assistants may also be (partly or fully) added in advance of the spray-drying. It is also possible in the course of the drying to only partly remove the solvent or suspension agent if the intention is to use it as a shaping assistant.

Instead of shaping the spray powder, optionally after adding shaping and, if appropriate, reinforcing assistants (including those in accordance with the invention), directly to the annular shaped unsupported catalyst precursor bodies (having curved and/or uncurved top surface of the rings), it is frequently appropriate to initially carry out an intermediate compaction in order to coarsen the powder (generally to a particle size of from 400 µm to 1 mm). Subsequently, the actual ring shaping is effected with the coarsened powder, and finely divided lubricant according to the invention may again be added beforehand if required.

Such an intermediate compaction for the purpose of particle coarsening may be effected, for example, by means of a compactor from Hosokawa Bepex GmbH (D-74211 Leingarten), of the K 200/100 compactor type. The hardness of the intermediate compactate is frequently already in the region of 10 N. Useful for the ring shaping to the shaped unsupported catalyst precursor body is, for example, a Kilian rotary tableting press (from Kilian in D-50735 Cologne) of the RX 73 or S 100 type. Alternatively, a tableting press from Korsch (D-13509 Berlin) of the PH 800-65 type may be used. Especially for preparing active compositions of the stoichiometry of the general formula II or III, it is advantageous to preform a mixed oxide $Y^1{}_{a'}Y^2{}_{b'}O_{x'}$ or $Bi_{a''}Z^2{}_{b''}O_{x''}$ as the source of the elements $Y^1$, $Y^2$ and $B^1$, $Z^2$ respectively in the absence of the remaining constituents of the active compositions of the stoichiometry of the general formula II or III and thus, after its preformation, as already described, to generate a finely divided shapeable mixture using sources of the remaining constituents of the active compositions of the stoichiometry of the general formula II or III, in order to shape therefrom, after adding shaping and, if appropriate, reinforcing assistants (including those in accordance with the invention), the annular shaped unsupported catalyst precursor bodies.

In such a procedure, care has to be taken merely that, in the case that the preparation of the finely divided shapeable mixture is effected in wet form (in suspension), the preformed mixed oxides $Y^1{}_aY^2{}_bO_{x'}$ or $Bi_{a''}Z^2{}_{b''}O_{x''}$ do not go into solution to a significant extent.

A preparation method as described above is described in detail in the documents DE-A 44 07 020, EP-A 835, EP-A 575 897 and DE-C 33 38 380.

For example, water-soluble salts of $Y^1$ such as nitrates, carbonates, hydroxides or acetates may be mixed in water with $Y^2$ acids or their ammonium salts, the mixture dried (preferably spray-dried) and the dried composition subsequently thermally treated. The thermally treated composition is subsequently appropriately comminuted (for example in a ball mill or by jet milling) and, from the powder which generally consists of substantially spherical particles and is obtainable in this way, the particle class having a largest particle diameter lying within the largest diameter range desired for the active composition of the stoichiometry of the general formula II or III is separated by classification to be carried out in a manner known per se (for example wet or dry screening) and is preferably mixed with, based on the mass of this separated particle class, from 0.1 to 3% by weight of finely divided $SiO_2$ (the particle diameter $d_{50}$ of the typically substantially spherical $SiO_2$ particles is appropriately from 100 nm to 15 μm), thus producing a starting composition 1. The thermal treatment is appropriately effected at temperatures of from 400 to 900° C., preferably from 600 to 900° C. The latter is especially true when the preformed mixed oxide is one of the stoichiometry $BiZ^2O_6$, $Bi_2Z^2{}_2O_9$ and/or $Bi_2Z^2{}_3O_{12}$, among which $Bi_2Z^2{}_2O_9$ is preferred, especially when $Z^2$=tungsten.

Typically, the thermal treatment is effected in an air stream (for example in a rotary tube furnace as described in DE-A 103 25 487). The duration of the thermal treatment generally extends to a few hours.

The remaining constituents of the desired active composition of the general formula II or III are normally used to prepare, starting from sources which are suitable in a manner known per se (cf. EP-A 835 and DE-C 33 38 380 and also DE-A 44 07 020), in an inventively appropriate manner, for example, a very intimate, preferably finely divided dry mixture (for example combining water-soluble salts such as halides, nitrates, acetates, carbonates or hydroxides in an aqueous solution and subsequently, for example, spray-drying the aqueous solution, or suspending water-insoluble salts, for example oxides, in aqueous medium and subsequently, for example, spray-drying the suspension) which is referred to here as starting composition 2. It is essential only that the constituents of the starting composition 2 are either already oxides or compounds which can be converted to oxides by heating, in the absence or presence of oxygen. Subsequently, the starting composition 1 and the starting composition 2 are mixed in the desired ratio in the inventive manner, i.e. after adding shaping and, if appropriate, reinforcing assistants (including those in accordance with the invention), to give the mixture which can be shaped to the annular shaped unsupported catalyst precursor body. The shaping may, as already described, appropriately from an application point of view, be effected by an intermediate compaction stage.

In a less preferred embodiment, the preformed mixed oxide $Y^1{}_aY^2{}_bO_{x'}$ or $Bi_{a''}Z^2{}_{b''}O_{x''}$ may also be intimately mixed with sources of the remaining constituents of the desired active composition in liquid, preferably aqueous, medium. This mixture is subsequently, for example, dried to give an intimate dry mixture and then, as already described, shaped and thermally treated. The sources of the remaining constituents may be dissolved and/or suspended in this liquid medium, whereas the preformed mixed oxide should be substantially insoluble, i.e. has to be suspended, in this liquid medium.

The preformed mixed oxide particles are present having a substantially unchanged longitudinal dimension established by the classification in the finished annular unsupported catalyst.

The specific surface area of mixed oxides $Y^1{}_aY^2{}_bO_{x'}$ or $Bi_{a''}Z^2{}_{b''}O_{x''}$ preformed in this way is preferably from 0.2 to 2 m²/g, more preferably from 0.5 to 1.2 m²/g. In addition, the total pore volume of mixed oxides preformed in this way advantageously results predominantly from micropores.

Advantageous relevant annular unsupported catalysts are those whose specific surface area O is from 5 to 20 or 15 m²/g, frequently from 5 to 10 m²/g. The total pore volume V of such annular unsupported catalysts is advantageously in the range from 0.1 to 1 or 0.8 cm³/g, frequently in the range from 0.2 to 0.4 cm³/g.

In general, shaped catalyst bodies prepared in accordance with the invention have a limited increase in that pore diameter $d^{max}$ whose pores having this diameter, in their entirety, make the greatest percentage contribution to the total pore volume of the shaped catalyst body prepared in accordance with the invention. This might be the cause of the increase, observed in accordance with the invention, in the target product selectivity achieved with shaped catalyst bodies prepared in accordance with the invention.

Typically, the side crushing strengths of annular unsupported catalysts obtainable as described are from 5 to 13 N, frequently from 8 to 11 N. These side crushing strengths of annular unsupported catalysts obtainable as described are normally also present when the remaining physical properties described as advantageous (for example O, V and pore diameter distribution) of annular unsupported catalysts obtainable as described are present.

As already mentioned, the annular unsupported catalysts obtainable as described are especially suitable as catalysts for the partial oxidation of propene to acrolein or of isobutene and/or tert-butanol to methacrolein. The partial oxidation may be carried out as described, for example, in the documents WO 00/53557, WO 00/53558, DE-A 199 10 506, EP-A 1106 598, WO 01/36364, DE-A 199 27 624, DE-A 199 48 248, DE-A 199 48 523, DE-A 199 48 241, EP-A 700 714, DE-A 10313213, DE-A 103 13 209, DE-A 102 32 748, DE-A 103 13 208, WO 03/039744, EP-A 279 374, DE-A 33 38 380, DE-A 33 00 044, EP-A 575 897, DE-A 10 2004 003 212, DE-A 10 2005 013 039, DE-A 10 2005 009 891, DE-A 10 2005 010 111, DE-A 10 2005 009 885 and DE-A 44 07 020, and the catalyst charge may comprise, for example, only annular unsupported catalysts obtainable as described or, for example, annular unsupported catalysts diluted with inert shaped bodies. In the latter case, the catalyst charge, advantageously, is generally configured in such a way that its volume-specific activity increases continuously, sharply and/or in stages in the flow direction of the reaction gas mixture.

The ring geometries of the unsupported catalysts obtainable as described emphasized individually in this document are found to be especially advantageous when the loading of the catalyst charge with propene, isobutene and/or tert-butanol (or its methyl ether) present in the starting reaction gas mixture is ≥130 l (STP)/l of catalyst charge h (upstream and/or downstream beds of pure inert material are not regarded as belonging to the catalyst charge in space velocity calculations). This is especially true when the other physical properties, described as advantageous in this document, of annular unsupported catalysts obtainable as described are also present.

However, this advantageous behavior of annular unsupported catalysts obtainable as described, in particular the aforementioned, is also present when the aforementioned loading of the catalyst charge is ≥140 l (STP)/l·h, or ≥150 l (STP)/l·h, or ≥160 l (STP)/l·h. Normally, the aforementioned loading of the catalyst charge will be ≤600 l (STP)/l·h, frequently ≤500 l (STP)/l·h, in many cases ≤400 l (STP)/l·h or ≤350 l (STP)/l·h. Hourly space velocities in the range from 160 l (STP)/l·h to 300 or 250 or 200 l (STP)/l·h are particularly typical.

It will be appreciated that the annular unsupported catalysts obtainable as described may also be used as catalysts for the partial oxidation of propene to acrolein or of isobutene and/or tert-butanol (or its methyl ether) to methacrolein at loadings of the catalyst charge with the starting compound to be partially oxidized of <130 l (STP)/l·h, or ≤120 l (STP)/l·h, or ≤110 l (STP)/l·h. However, this loading will generally be at values of ≥60 l (STP)/l·h, or ≥70 l (STP)/l·h, or ≥80 l (STP)/l·h.

In principle, the loading of the catalyst charge with the starting compound to be partially oxidized (propene, isobutene and/or tert-butanol (or its methyl ether)) may be adjusted using two adjusting screws:
a) the loading of the catalyst charge with starting reaction gas mixture; and/or
b) the content in the starting reaction gas mixture of the starting compound to be partially oxidized.

The annular unsupported catalysts obtainable in accordance with the invention are also especially suitable when, at loadings of the catalyst charge with the organic compound to be partially oxidized which are above 130 l (STP)/l·h, the loading is adjusted in particular using the aforementioned adjusting screw a).

The propene fraction (isobutene fraction or tert-butanol fraction (or its methyl ether fraction)) in the starting reaction gas mixture will generally be (i.e. essentially irrespective of the loading) from 4 to 20% by volume, frequently from 5 to 15% by volume, or from 5 to 12% by volume, or from 5 to 8% by volume (based in each case on the total volume).

Frequently, the process of the partial oxidation catalyzed by the annular unsupported catalysts obtainable as described will be carried out (essentially irrespective of the loading) at an (organic) compound to be partially oxidized (e.g. propene): oxygen:inert gases (including steam) volume ratio in the starting reaction gas mixture of from 1:(1.0 to 3.0):(5 to 25), preferably 1:(1.5 to 2.3):(10 to 20).

Inert gases refer to those gases of which at least 95 mol %, preferably at least 98 mol %, remain chemically unchanged in the course of the partial oxidation.

In the above-described starting reaction gas mixtures, the inert gas may consist of ≥20% by volume, or ≥30% by volume, or ≥40% by volume, or ≥50% by volume, or ≥60% by volume, or ≥70% by volume or ≥80% by volume, or ≥90% by volume or ≥95% by volume, of molecular nitrogen.

However, when the loadings of the catalyst charge with the organic compound to be partially oxidized are ≥150 l (STP)/l·h, it is recommended to use inert diluent gases such as propane, ethane, methane, pentane, butane, $CO_2$, CO, steam and/or noble gases for the starting reaction gas mixture. Generally, these inert gases and their mixtures may also be used even at lower inventive loadings of the catalyst charge with the organic compound to be partially oxidized. Cycle gas may also be used as a diluent gas. Cycle gas refers to the residual gas which remains when the target compound is substantially selectively removed from the product gas mixture of the partial oxidation. It has to be taken into account that the partial oxidations to acrolein or methacrolein using the obtainable annular unsupported catalysts may only be the first stage of a two-stage partial oxidation to acrylic acid or methacrylic acid as the actual target compounds, so that the cycle gas is then not usually formed until after the second stage. In such a two-stage partial oxidation, the product gas mixture of the first stage is generally fed as such, optionally after cooling and/or secondary oxygen addition, to the second partial oxidation stage.

In the partial oxidation of propene to acrolein using the annular unsupported catalysts obtainable as described, a typical composition of the starting reaction gas mixture measured at the reactor inlet (irrespective of the loading selected) may comprise, for example, the following components:

| | |
|---|---|
| from 6 to 6.5% by volume of | propene, |
| from 1 to 3.5% by volume of | $H_2O$, |
| from 0.2 to 0.5% by volume of | CO, |
| from 0.6 to 1.2% by volume of | $CO_2$, |
| from 0.015 to 0.04% by volume of | acrolein, |
| from 10.4 to 11.3% by volume of | $O_2$ and, | as the remainder ad 100%, molecular nitrogen,
or:

| | |
|---|---|
| 5.6% by volume of | propene, |
| 10.2% by volume of | oxygen, |
| 1.2% by volume of | $CO_x$, |
| 81.3% by volume of | $N_2$ and |
| 1.4% by volume of | $H_2O$. |

The former compositions are suitable especially at propene loadings of ≥130 l (STP)/l·h and the latter composition especially at propene loadings of <130 l (STP)/l·h, especially ≤100 l (STP)/l·h.

As alternative compositions of the starting reaction gas mixture, useful compositions (irrespective of the loading selected) are those which have the following components:

| | |
|---|---|
| from 4 to 25% by volume of | propylene, |
| from 6 to 70% by volume of | propane, |
| from 5 to 60% by volume of | $H_2O$, |
| from 8 to 65% by volume of | $O_2$, and |
| from 0.3 to 20% by volume of | $H_2$; | or

| | |
|---|---|
| from 4 to 25% by volume of | propylene, |
| from 6 to 70% by volume of | propane, |
| from 0 to 60% by volume of | $H_2O$, |
| from 8 to 16% by volume of | $O_2$, |
| from 0 to 20% by volume of | $H_2$, |
| from 0 to 0.5% by volume of | CO, |
| from 0 to 1.2% by volume of | $CO_2$, |
| from 0 to 0.04% by volume of | acrolein, | and, as the remainder ad 100% by volume, essentially $N_2$;
or

| | |
|---|---|
| from 50 to 80% by volume of | propane, |
| from 0.1 to 20% by volume of | propylene, |
| from 0 to 10% by volume of | $H_2$, |
| from 0 to 20% by volume of | $N_2$, and |
| from 5 to 15% by volume of | $H_2O$; | sufficient molecular oxygen that the molar ratio of oxygen content to propylene content is from 1.5 to 2.5.
or

| | |
|---|---|
| from 6 to 9% by volume of | propylene, |
| from 8 to 18% by volume of | molecular oxygen, |
| from 6 to 30% by volume of | propane, and |
| from 32 to 72% by volume of | molecular nitrogen. |

However, the starting reaction gas mixture may also have the following composition:

| | |
|---|---|
| from 4 to 15% by volume of | propene, |
| from 1.5 to 30% by volume | (frequently from 6 to 15% by volume) of water, |
| from ≥0 to 10% by volume | (preferably from ≥0 to 5% by volume) of constituents other than propene, water, oxygen and nitrogen, and sufficient molecular oxygen that the molar ratio of molecular oxygen present to molecular propene present is from 1.5 to 2.5, and, as the remainder up to 100% by volume of the total amount of molecular nitrogen. |

Another possible starting reaction gas mixture composition may comprise:

| | |
|---|---|
| 6.0% by volume of | propene, |
| 60% by volume of | air and |
| 34% by volume of | $H_2O$. |

Alternatively, starting reaction gas mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used.

The annular catalysts obtainable as described are also suitable for the processes of DE-A 10246119 and DE-A 10245585.

Further starting reaction gas mixtures which are suitable in accordance with the invention may lie within the following composition framework:

| | |
|---|---|
| from 7 to 11% by volume of | propene, |
| from 6 to 12% by volume of | water, |
| from ≥0 to 5% by volume of | constituents other than propene, water, oxygen and nitrogen, | sufficient molecular oxygen that the molar ratio of oxygen present to molecular propene present is from 1.6 to 2.2, and as the remainder up to 100% by volume of the total amount of molecular nitrogen.

In the case of methacrolein as the target compound, the starting reaction gas mixture may in particular have the composition described in DE-A 44 07 020.

The reaction temperature for the propene partial oxidation when the annular unsupported catalysts obtainable as described are used is frequently from 300 to 380° C. The same also applies in the case of methacrolein as the target compound.

The reaction pressure for the aforementioned partial oxidations is generally from 0.5 or 1.5 to 3 or 4 bar (what are meant in this document, unless explicitly stated otherwise, are absolute pressures).

The total loading of the catalyst charge with starting reaction gas mixture in the aforementioned partial oxidations typically amounts to from 1000 to 10 000 l (STP)/l·h, usually to from 1500 to 5000 l (STP)/l·h and often to from 2000 to 4000 l (STP)/l·h.

The propene to be used in the starting reaction gas mixture is in particular polymer-grade propene and chemical-grade propene, as described, for example, in DE-A 102 32 748.

The oxygen source used is normally air.

In the simplest case, the partial oxidation employing the annular unsupported catalysts obtainable as described may be carried out, for example, in a one-zone multiple catalyst tube fixed bed reactor, as described by DE-A 44 31 957, EP-A 700 714 and EP-A 700 893.

Typically, the catalyst tubes in the aforementioned tube bundle reactors are manufactured from ferritic steel and typically have a wall thickness of from 1 to 3 mm. Their internal diameter is generally from 20 to 30 mm, frequently from 21 to 26 mm. A typical catalyst tube length is, for example, 3.20 m. It is appropriate from an application point of view for the number of catalyst tubes accommodated in the tube bundle vessel to be at least 5000, preferably at least 1000. Frequently, the number of catalyst tubes accommodated in the reaction vessel is from 15 000 to 35 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes from immediately adjacent catalyst tubes (known as the catalyst tube pitch) is from 35 to 45 mm (cf. EP-B 468 290).

However, the partial oxidation may also be carried out in a multizone (for example two-zone) multiple catalyst tube fixed bed reactor, as recommended by DE-A 199 10 506, DE-A 103 13 213, DE-A 103 13 208 and EP-A 1 106 598, especially at elevated loadings of the catalyst charge with the organic compound to be partially oxidized. A typical catalyst tube length in the case of a two-zone multiple catalyst tube fixed bed reactor is 3.50 m. Everything else is substantially as described for the one-zone multiple catalyst tube fixed bed reactor. Around the catalyst tubes, within which the catalyst charge is disposed, a heat exchange medium is conducted in each heating zone. Useful such media are, for example, melts of salts such as potassium nitrate, potassium nitrite, sodium nitrite and/or sodium nitrate, or of low-melting metals such as sodium, mercury and also alloys of different metals. The flow rate of the heat exchange medium within the particular heating zone is generally selected in such a way that the temperature of the heat exchange medium rises from the entry point into the temperature zone to the exit point from the temperature zone by from 0 to 15° C., frequently from 1 to 10° C., or from 2 to 8° C., or from 3 to 6° C.

The entrance temperature of the heat exchange medium which, viewed over the particular heating zone, may be conducted in cocurrent or in countercurrent to the reaction gas mixture is preferably selected as recommended in the documents EP-A 1 106 598, DE-A 199 48 523, DE-A 199 48 248, DE-A 103 13 209, EP-A 700 714, DE-A 103 13 208, DE-A 103 13 213, WO 00/53557, WO 00/53558, WO 01/36364, WO 00/53557 and also the other documents cited as prior art in this document. Within the heating zone, the heat exchange medium is preferably conducted in a meandering manner. In general, the multiple catalyst tube fixed bed reactor additionally has thermal tubes for determining the gas temperature in the catalyst bed. Appropriately, the internal diameter of the thermal tubes and the diameter of the internal accommodating sleeve for the thermal element are selected in such a way that the ratio of volume developing heat of reaction to surface area removing heat for the thermal tubes and working tubes is the same or only slightly different.

The pressure drop in the case of working tubes and thermal tubes, based on the same GHSV, should be the same. A pressure drop may be equalized in the case of the thermal tube by adding spalled catalyst to the shaped catalyst bodies. This equalization is appropriately effected homogeneously over the entire thermal tube length.

To prepare the catalyst charge in the catalyst tubes, as already mentioned, it is possible only to use annular unsupported catalysts obtainable as described or, for example also substantially homogeneous mixtures of annular unsupported catalysts obtainable as described and shaped bodies which have no active composition and behave substantially inertly with respect to the heterogeneously catalyzed partial gas phase oxidation. Useful materials for such inert shaped bodies include, for example, porous or nonporous aluminum oxides, silicon dioxide, zirconium dioxide, silicon carbide, silicates such as magnesium or aluminum silicate or steatite (for example of the C220 type from CeramTec, Germany).

The geometry of such inert shaped diluent bodies may in principle be as desired. In other words, they may be, for example, spheres, polygons, solid cylinders or else, like the shaped catalyst bodies, rings. Frequently, the inert shaped diluent bodies selected will be those whose geometry corresponds to that of the shaped catalyst bodies to be diluted with them. However, along the catalyst charge, the geometry of the shaped catalyst body may also be changed or shaped catalyst bodies of different geometry may be used in a substantially homogeneous mixture. In a less preferred procedure, the active composition of the shaped catalyst body may also be changed along the catalyst charge.

Quite generally, as already mentioned, the catalyst charge is advantageously configured in such a way that the volume-specific (i.e. normalized to the unit of the volume) activity either remains constant or increases (continuously, sharply or stepwise) in the flow direction of the reaction gas mixture.

A reduction in the volume-specific activity may be achieved in a simple manner, for example, by homogeneously diluting a basic amount of annular unsupported catalysts prepared uniformly in accordance with the invention with inert shaped diluent bodies. The higher the proportion of the shaped diluent bodies selected, the lower the active composition or catalyst activity present in a certain volume of the charge. However, a reduction can also be achieved by changing the geometry of the annular unsupported catalysts obtainable according to the invention in such a way that the amount of active composition present in the unit of the total ring volume (including the ring orifice) becomes smaller.

For the heterogeneously catalyzed gas phase partial oxidations using the annular unsupported catalysts obtainable as described, the catalyst charge is preferably either configured uniformly with only one unsupported catalyst ring over the entire length or structured as follows. At the reactor inlet is positioned, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of the catalyst charge, a substantially homogeneous mixture of annular unsupported catalyst obtainable according to the invention and inert shaped diluent bodies (both preferably having substantially the same geometry), the proportion by weight of the shaped diluent bodies (the mass densities of shaped catalyst bodies and of shaped diluent bodies generally differ only slightly) being normally from 5 to 40% by weight, or from 10 to 40% by weight, or from 20 to 40% by weight, or from 25 to 35% by weight. Downstream of this first charge section, there is then advantageously, up to the end of the length of the catalyst charge (i.e., for example, to a length of from 1.00 to 3.00 m or from 1.00 to 2.70 m, preferably from 1.40 to 3.00 m or from 2.00 to 3.00 m), either a bed of the annular unsupported catalyst obtainable as described which is diluted only to a lesser extent (than in the first section), or, most preferably, an unaccompanied (undiluted) bed of the same annular unsupported catalyst which has also been used in the first section. Of course, a constant dilution may also be selected over the entire charge. Charging may also be effected in the first section using only an annular unsupported catalyst obtainable according to the invention and having lower active composition density based on its space demand, and, in the second section, using an annular unsupported catalyst obtainable according to the invention having higher active composition density based on its space demand (for example 6.5 mm×3 mm×4.5 mm [E×H×I] in the first section, and 5×2×2 mm in the second section).

Overall, in a partial oxidation for preparing acrolein or methacrolein carried out using the annular unsupported catalysts obtainable as described as catalysts, the catalyst charge, the starting reaction gas mixture, the loading and the reaction temperature are generally selected in such a way that, on single pass of the reaction gas mixture through the catalyst charge, a conversion of the organic compound to be partially oxidized (propene, isobutene, tert-butanol or its methyl ether) of at least 90 mol %, or 92 mol %, preferably of at least 94 mol %, results. The selectivity of acrolein or methacrolein formation will regularly be ≥80 mol %, or ≥85 mol %. Of course, very low hotspot temperatures are desired.

Overall, the annular unsupported catalysts obtainable as described bring about an increased selectivity of target product formation.

Finally, it is emphasized that the annular unsupported catalysts obtainable as described also have advantageous fracture behavior in the course of reactor charging. Their pressure drop behavior is also advantageous. Otherwise, the annular unsupported catalysts obtainable as described are quite generally suitable as catalysts having increased selectivity for catalytic partial oxidations in the gas phase of organic compounds such as lower (for example comprising from 3 to 6 (i.e. 3, 4, 5, or 6) carbon atoms) alkanes (in particular propane), alkanols, alkanals, alkenes and alkenals to olefinically unsaturated aldehydes and/or carboxylic acids, and also the appropriate nitriles (ammoxidation, in particular of propene to acrylonitrile and of 2-methylpropene or tert-butanol (or its methyl ether) to methacrylonitrile) and also for catalytic oxidative dehydrogenations in the gas phase of organic compounds (for example comprising 3, 4, 5, or 6 carbon atoms).

Particularly advantageous stoichiometries for the process of propylene partial oxidation to acrolein are:
a) $[Bi_2W_2O_9 \cdot 2WO_3]_{0.5}[Mo_{12}Co_{5.5}Fe_{2.94}Si_{1.59}K_{0.08}O_x]_1$;
b) $Mo_{12}Ni_{6.5}Zn_2Fe_2Bi_1P_{0.0065}K_{0.06}O_x \cdot 10SiO_2$;
c) $Mo_{12}CO_7Fe_{2.94}Bi_{0.6}Si_{1.59}K_{0.08}O_x$;
d) as per multimetal oxide II unsupported catalyst according to Example 1 of DE-A 197 46 210; and
e) as per Example 1c of EP-A 015 565.

The bismuth content of the active compositions as described may also be adjusted as described in DE-A 100 63 162. In this method, a solution or suspension is generated from starting compounds of the elemental constituents of the desired active composition, said solution or suspension comprising the total amount of elemental constituents other than Bi required to prepare the active composition, but only a portion of the Bi required to prepare the active composition, the solution or suspension is dried to obtain a dry mass and the remaining amount of Bi additionally required to prepare the active composition is incorporated into this dry mass in the form of a starting compound of Bi, as described in DE-A 100

63 162, to obtain a shapeable mixture (for example as in the example of DE-A 100 63 162), the shapeable mixture is shaped to an annular shaped unsupported catalyst body in the inventive manner (i.e. after adding shaping and, if appropriate, reinforcing assistants), and this is then converted to the desired annular unsupported catalyst by thermal treatment (for example as in the example in DE-A 100 63 162). The stoichiometries (especially of the examples) and thermal treatment conditions of this (aforementioned) document are likewise particularly suitable for propylene partial oxidation to acrolein. This is especially true of the stoichiometry $Mo_{12}Bi_{1.0}Fe_3Co_7Si_{1.6}K_{0.08}$.

The start-up of a fresh catalyst charge comprising annular unsupported catalysts obtainable as described may be effected as described in DE-A 10337788. In general, activity and selectivity of the target product formation initially increase with the operating time of the catalyst charge. This conditioning may be accelerated by carrying it out at substantially uniform conversion under increased loading of the catalyst charge with starting reaction gas mixture, and, after substantially completed conditioning, reducing the loading to its target value.

The present invention further comprises in particular a process for preparing annular shaped catalyst bodies with curved and/or uncurved top surface of the rings, whose active composition has a stoichiometry of the general formula IV

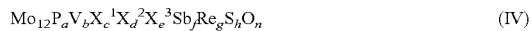

$$Mo_{12}P_aV_bX_c^1X_d^2X_e^3Sb_fRe_gS_hO_n \quad (IV)$$

in which the variables are each defined as follows:
$X^1$=potassium, rubidium and/or cesium,
$X^2$=copper and/or silver,
$X^3$=cerium, boron, zirconium, manganese and/or bismuth,
a=0.5 to 3,
b=0.01 to 3,
c=0.2 to 3,
d=0.01 to 2,
e=0 to 2,
f=0.01 to 2,
g=0 to 1,
h=0.001 to 0.5 and
n=a number which is determined by the valency and frequency of the elements in IV other than oxygen,
and whose annular geometry corresponds to that of the annular shaped catalyst bodies already described with active compositions of a stoichiometry of the general formula (I), (II) or (III).

Preference is given to active compositions IV in which h is from 0.03 to 0.5.

Particularly preferred stoichiometry of the general formula IV is that of the Working Examples B1 to B15 from EP-A 467 144, even when these exemplary active compositions do not comprise any K and/or any Re.

The aforementioned EP-A 467 144 also describes the preparation of such annular shaped catalyst bodies and their use as catalysts for the heterogeneously catalyzed gas phase partial oxidation of methacrolein to methacrylic acid. These descriptions also apply in the context given in the present application, apart from the fact that graphite is to be used in accordance with the invention as a lubricant in the preparation of the annular shaped catalyst bodies.

In other words, annular shaped catalyst bodies with active compositions of the general stoichiometry IV can be prepared by finely dividing salts, suitable as starting compounds, of the elemental constituents constituting them, if appropriate at elevated temperature and with addition of acids or bases, in aqueous medium by dissolution and/or suspension, and mixing them, if appropriate under inert gas to avoid undesired oxidation processes, drying the mixture (for example concentrating it by evaporation or spray-drying it), adding the graphite required in accordance with the invention and, if appropriate, others of the shaping assistants and reinforcing assistants mentioned to the resulting dry mass in finely divided form or having been converted to finely divided form, shaping (compacting) the resulting finely divided mass to the desired ring geometry and subsequently treating the resulting shaped catalyst precursor bodies thermally. Preference is given to carrying out the thermal treatment at temperatures of from 180 to 480° C., more preferably at temperatures of from 250 to 450° C. The thermal treatment can be effected under the gas atmospheres already described. Mention should be made by way of example once again of flowing air, flowing inert atmosphere (for example $N_2$, or $CO_2$, or noble gases) or reduced pressure. The thermal treatment can be carried out in a plurality of temperature stages and/or in various atmospheres. For example, it is possible to treat thermally at from 200 to 260° C. in air in a first stage, at from 420 to 460° C. in nitrogen in a second stage and at from 350 to 410° C. again in air in a third stage. In general, flowing air is the preferred atmosphere for the thermal treatment.

Otherwise, the statements made for the preparation of annular shaped catalyst bodies of active compositions (I), (II) and (III) apply here in a corresponding manner, except with the difference that the increased side crushing strengths are preferred here for the annular shaped unsupported catalyst precursor bodies.

In other words, for example, a preferred drying process for the aqueous solution or suspension of the sources of the elemental constituents of the desired active composition is spray-drying. The resulting spray powder with a particle diameter $d_{50}$ between 10 and 50 μm is advantageously in accordance with the invention, and appropriately in accordance with the invention after addition of finely divided graphite as an assistant, intermediately compacted in order to coarsen the powder. Preference is given to effecting the intermediate compaction here to particle diameters of from 100 to 2000 μm, preferably from 150 to 1500 μm and more preferably from 400 to 1000 μm. Subsequently, the actual shaping is effected on the basis of the coarsened powder, and it is possible if required again to add finely divided inventive graphite (and, if appropriate, further shaping and/or reinforcing assistants) beforehand. The statements made on the side crushing strengths for the preparation of the annular shaped catalyst bodies of the active compositions (I), (II) and (III) apply here analogously.

In the preparation method described of annular shaped catalyst bodies from active compositions of the general formula IV, antimony is used typically in the form of antimony trioxide, rhenium for example, in the form of rhenium(VII) oxide, molybdenum preferably in the form of the ammonium salt of molybdic acid or phosphomolybdic acid, boron, for example, in the form of boric acid, vanadium generally in the form of ammonium vanadate or vanadium oxalate, phosphorus advantageously in the form of orthophosphoric acid or diammonium phosphate, sulfur, for example, in the form of ammonium sulfate, and the cationic metals normally in the form of the nitrates, oxides, hydroxides, carbonates, chlorides, formates, oxalates and/or acetates or the hydrates thereof. Preferred ring geometry of the finished shaped catalyst body here is the geometry 7 mm×7 mm×3 mm (external diameter×length×internal diameter). The catalytic gas phase oxidation of methacrolein to methacrylic acid using the annular shaped catalyst bodies obtainable as described can be effected in a manner known per se, for example that described in EP-A 467 144. The oxygen oxidant can be used, for example, in the form of air, but also in pure form. Owing to the high heat of reaction, the reactants are preferably diluted with inert gases such as $N_2$, CO, $CO_2$ and/or with steam. Preference is given to working at a methacrolein:oxygen:steam: inert gas ratio of 1:(1 to 3):(2 to 20):(3 to 30), more preferably of 1:(1 to 3):(3 to 10):(7 to 18). The proportion of methacrolein in the starting reaction gas mixture varies generally from 4 to 11% by volume, in many cases from 4.5 to 9% by volume. To avoid explosive mixtures, the oxygen content is preferably restricted to ≤12.5% by volume. This is more preferably achieved by recycling a substream of the offgas removed from the reaction product. Otherwise, the gas phase partial oxidation to methacrylic acid is typically effected at total spatial loadings on the fixed catalyst bed of from 600 to 1800 l (STP)/l·h, or at methacrolein loadings of from 40 to 100 l (STP)/l·h. The reactor used is generally a tube bundle reactor. Reaction gas and salt bath can, viewed over the reactor, be conducted either in cocurrent or in countercurrent. The salt bath itself is normally conducted through the reactor in meandering form. Preferred graphite for preparing annular shaped catalyst bodies composed of active compositions of the general stoichiometry IV is Asbury 3160 and/or Asbury 4012.

The process according to the invention also comprises in particular a process for preparing annular shaped catalyst bodies with curved and/or uncurved top surface of the rings, whose active composition is a multielement oxide comprising vanadium, phosphorus and oxygen, and which are suitable as catalysts for the heterogeneously catalyzed gas phase oxidation of at least one hydrocarbon having at least four carbon atoms (especially n-butane, n-butene and/or benzene) to maleic anhydride. The stoichiometry of the multielement oxide composition may then, for example, be one of the general formula V $$V_1P_bFe_cX^1{}_dX^2{}_eO_n \qquad (V)$$

in which the variables are each defined as follows:
$X^1$=Mo, Bi, Co, Ni, Si, Zn, Hf, Zr, Ti, Cr, Mn, Cu, B, Sn and/or Nb,
$X^2$=K, Na, Rb, Cs and/or Tl,
b=0.9 to 1.5,
c=0 to 0.1,
d=0 to 0.1,
e=0 to 0.1, and
n=a number which is determined by the valency and frequency of the elements in V other than oxygen.

The preparation of corresponding annular shaped catalyst bodies is described in WO 03/078310 with addition of graphite, which is not specified in more detail, as a shaping assistant. All remarks of WO 03/078310 and all catalysts addressed in WO 03/078310 are viable and usable as addressed in WO 03/078310 even when the preparation measures disclosed in WO 03/078310 are retained, and the graphite used in the preparation is replaced by amounts of inventive graphite of identical weight. However, the selectivity of target product formation is enhanced. In other words, even in the present case of the annular multielement oxide catalysts comprising vanadium, phosphorus and oxygen, the inventive advantages are established. This is true in particular of all working examples of WO 03/078310. By increasing the graphite content (the amount of graphite used) to from 5 to 35% by weight, its pore-forming properties can be enhanced if appropriate, and the selectivity or target product formation can be increased further.

The statements made above for the multimetal oxide catalysts comprising vanadium, phosphorus and oxygen of WO 03/078310 and their use apply correspondingly to those of WO 01/68245 and to those of DE-A 10 2005 035 978. According to the invention, the latter are thus preparable as follows:
a) reaction of a pentavalent vanadium compound (e.g. $V_2O_5$) with an organic reducing solvent (e.g. isobutanol) in the presence of a pentavalent phosphorus compound (e.g. ortho- and/or pyrophosphoric acid) with heating to from 75 to 205° C., preferably to from 100 to 120° C.;
b) cooling the reaction gas mixture to advantageously from 40 to 90° C.;
c) adding iron(III) phosphate;
d) reheating to from 75 to 205° C., preferably from 100 to 120° C.;
e) isolating the vanadium-, phosphorus-, iron- and oxygen-comprising solid precursor mass formed (for example by filtration);
f) drying and/or thermally pretreating the precursor mass (if appropriate until commencement of preformation by elimination of water from the precursor mass);
g) inventive addition of graphite and shaping by conversion to a, for example, spherical, annular or cylindrical structure;
h) thermally treating the shaped catalyst precursor bodies formed by heating in an atmosphere which comprises oxygen, nitrogen, noble gases, carbon dioxide, carbon monoxide and/or steam, for example as described in WO 03078310 on page 20 line 16 to page 21 line 35.

The process according to the invention also comprises in particular processes for preparing inventive, for example spherical, solid cylindrical or annular shaped catalyst bodies with curved and/or uncurved top surface of the rings, whose active composition is a multimetal oxide comprising Mo, V and at least one of the elements Te and Sb, as described, for example, in the documents EP-A 962 253, DE-A 101 22 027, EP-A 608 838, DE-A 198 35 247, EP-A 895 809, EP-A 1 254 709, EP-A1 192 987, EP-A 1 262 235, EP-A 1 193 240, JP-A 11-343261, JP-A 11-343262, EP-A 1 090 684, EP-A 1 301 457, EP-A 1 254 707, EP-A 1 335 793, DE-A 100 46 672, DE-A 100 34 825, EP-A 1 556 337, DE-A 100 33 121, WO 01/98246, EP-A 1 558 569.

Frequently, the aforementioned multimetal oxide compositions also comprise the element Nb. The aforementioned multimetal oxide catalysts are suitable in inventive preparation for all heterogeneously catalyzed gas phase reactions carried out in the aforementioned documents. These are in particular the heterogeneously catalyzed partial gas phase oxidation of propane to acrylic acid and of acrolein to acrylic acid, of methacrolein to methacrylic acid and of isobutane to methacrylic acid.

Finally, it should also be emphasized at this point that shaped catalyst bodies prepared in accordance with the invention do not necessarily have to be used as such as catalysts for heterogeneously catalyzed gas phase reactions. Instead, they can be subjected to grinding and, after classification of the resulting finely divided material, applied with the aid of a suitable liquid binder to the surface of a suitable support body. After drying or directly after application of the active composition coating to the support body, the resulting coated catalyst can be used as a catalyst for heterogeneously catalyzed gas phase reactions, as described, for example, in DE-A 101 22 027.

In summary, it should be emphasized once again that the shaped catalyst bodies obtainable in accordance with the invention are outstandingly suitable as catalysts for heterogeneously catalyzed reactions in the gas phase with increased selectivity of target product formation. These gas phase reactions include in particular the partial oxidations of organic compounds, the partial ammoxidations of organic compounds and the oxydehydrogenations of organic compounds. Useful partial heterogeneously catalyzed oxidations of organic compounds include in particular those mentioned in DE-A 10 2004 025 445. Mention should once again be made by way of example of the conversion of propylene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf. for example, DE-A 25 26 238, EP-A 092 097, EP-A 58927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene, p-xylene or naphthalene to phthalic anhydride (cf., for example, EP-A 522 871) or the corresponding acids, and also the conversion of butadiene to maleic anhydride (cf., for example, DE-A 21 06 796 and DE-A 16 24 921), the conversion of n-butane to maleic anhydride (cf., for example, GB-A 1 464 198 and GB-A 1 291 354), the conversion of indenes to, for example, anthraquinone (cf., for example, DE-A 20 25 430), the conversion of ethylene to ethylene oxide or of propylene to propylene oxide (cf., for example, DE-B 12 54 137, DE-A 21 59 346, EP-A 372 972, WO 89/07101, DE-A 43 11 608 and Beyer, Lehrbuch der organischen Chemie [Textbook of organic chemistry], 17th Edition (1973), Hirzel Verlag, Stuttgart, p. 261), the conversion of propylene and/or acrolein to acrylonitrile (cf., for example, DE-A 23 51 151), the conversion of isobutene and/or methacrolein to methacrylonitrile (i.e., in this document, the term partial oxidation shall, as already stated also comprise partial ammoxidation, i.e. partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 101 31 297, EP-A 1 090 684, EP-A 608 838, DE-A 100 46 672, EP-A 529 853, WO 01/96270 and DE-A 100 28 582), and also the reactions of ethane to give acetic acid, of benzene to give phenol, and of hydrocarbons having 4 carbon atoms to give the corresponding butanediols or to give butadiene.

It will be appreciated that the gas phase reaction may also be a heterogeneously catalyzed hydrogenation or a heterogeneously catalyzed dehydrogenation of organic compounds.

EXAMPLES E AND COMPARATIVE EXAMPLES C

A) Preparation of annular shaped unsupported catalyst bodies with the subsequent stoichiometry of the active composition and using different graphites as shaping assistants:

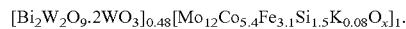

$[Bi_2W_2O_9 \cdot 2WO_3]_{0.48}[Mo_{12}Co_{5.4}Fe_{3.1}Si_{1.5}K_{0.08}O_x]_1$.

1. Preparation of a Starting Composition 1

214.7 kg of tungstic acid at 25° C. (74.1% by weight of W, H.C. Starck, D-38615 Goslar, purity >99.9% by weight of $WO_3$ after ignition at 750° C., 0.4 μm<$d_{50}$<0.8 μm) was stirred (70 rpm) in portions at 25° C. into 780 kg of an aqueous bismuth nitrate solution in nitric acid at 25° C. (11.2% by weight of Bi; free nitric acid from 3 to 5% by weight; bulk density: 1.22 to 1.27 g/ml, prepared with nitric acid from bismuth metal from Sidech S.A., 1495 Tilly, Belgium, purity: >99.997% by weight of Bi, <7 mg/kg of Pb, in each case <5 mg/kg of Ni, μg, Fe, in each case <3 mg/kg of Cu, Sb, and <1 mg/kg of Cd, Zn) at 25° C. within 20 min. The resulting aqueous mixture was subsequently stirred at 25° C. for another 3 h and then spray-dried.

Spray-drying is effected in a rotary-disk spray tower in hot air countercurrent at a gas inlet temperature of 300±10° C., a gas outlet temperature of 100±10° C., a disk speed of 18 000 rpm and a throughput of 200 l/h. The resulting spray powder, whose particle size was essentially between 5 and 30 μm and which had an ignition loss of 12.8% by weight (calcine at 600° C. for 3 h under air) was subsequently converted to a paste with 16.7% by weight (based on the powder) of water at 25° C. in a kneader (20 rpm) for 30 min and extruded by means of an extruder (torque: ≤50 Nm) to extrudates of diameter 6 mm. These were cut into sections of 6 cm, dried on a three-zone belt dryer with a residence time of 120 min per zone at temperatures of 90-95° C. (zone 1), 115° C. (zone 2) and 125° C. (zone 3) under air, and then treated thermally at a temperature in the region of 830° C. (calcined; in a rotary tube oven with airflow (reduced pressure 0.3 mbar, internal volume 1.54 m³, 200 m³ (STP)/h of air, 50 kg/h of extrudate, speed: 1 rpm)). What is important in the precise setting of the calcination temperature is that it has to be oriented to the desired phase composition of the calcination product. The $WO_3$ (monoclinic) and $Bi_2W_2O_9$ (orthorhombic) phases are desired; the presence of γ-$Bi_2WO_6$ (russellite) is undesired. Should, therefore, after the calcination, the compound γ-$Bi_2WO_6$ still be detectable on the basis of a reflection in the X-ray powder diffractogram at a reflection of 2Θ=28.4° (CuKα radiation), the preparation should be repeated and the calcination temperature within the temperature range specified or the residence time at the same calcination temperature should be increased until the disappearance of the reflection is achieved. The preformed calcined mixed oxide thus obtained was ground at 2500 rpm with a BQ500 Biplex mill, such that the $d_{50}$ value was 2.45 μm ($d_{10}$=1.05 μm, $d_{90}$=5.92 μm) and the BET surface area was 0.8 m²/g.

The grinding material was then mixed in portions of 5 kg in an Eirich intensive mixer (RO2, fill volume: 3-5 I, 1.9 kW, Maschinenfabrik Gustav Eirich GmbH & Co KG, D-74736 Hardheim) with bladed heads rotating counter to the turntable (turntable speed 50 rpm, bladed head speed: 2500 rpm) homogeneously within 5 min with 0.5% by weight (based on the grinding material) of finely divided $SiO_2$ from Degussa of the Sipernat® D17 type (tapped density 150 g/l; $d_{50}$ value of the $SiO_2$ particles (laser diffraction to ISO 13320-1) was 10 μm, the specific surface area (nitrogen adsorption to ISO 5794-1, Annex D) was 100 m²/g).

2. Preparation of a Starting Composition 2

A solution A was prepared by metering 1.075 kg of an aqueous potassium hydroxide solution at 60° C. (47.5% by weight of KOH) and then, with a metering rate of 600 kg/h, 237.1 kg of ammonium heptamolybdate tetrahydrate (white crystals having a particle size d of <1 mm, 81.5% by weight of $MoO_3$, 7.0-8.5% by weight of $NH_3$, max. 150 mg/kg of alkali metals, H.C. Starck, D-38642 Goslar) at 60° C. with stirring (70 rpm) to 660 l of water at a temperature of 60° C. within one minute, and stirring the resulting slightly cloudy solution at 60° C. for 60 min.

A solution B was prepared by initially charging, at 60° C., 282.0 kg of an aqueous cobalt(II) nitrate solution at a temperature of 60° C. (12.5% by weight of Co, prepared with nitric acid from cobalt metal from MFT Metals & Ferro-Alloys Trading GmbH, D-41747 Viersen, purity: >99.6% by weight, <0.3% by weight of Ni, <100 mg/kg of Fe, <50 mg/kg of Cu) and metering thereto, with stirring (70 rpm), 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal). Subsequently, while maintaining the 60° C., the mixture was stirred for a further 30 minutes. Then, while retaining the 60° C., solution B was discharged into initially charged solution A and the mixture was stirred at 60° C. for a further 15 minutes. Subsequently, 19.9 kg of silica gel from Du Pont of the Ludox type (49.1% by weight of $SiO_2$, density: 1.29 g/ml, pH from 8.5 to 9.5, alkali metal content max. 0.5% by weight) were added to the resulting aqueous mixture which was then stirred at 60° C. for a further 15 minutes.

Subsequently, the product was spray-dried in a rotary-disk spray tower in a hot air countercurrent (gas inlet temperature: 350±10° C., gas outlet temperature: 140±5° C., disk speed: 18 000 rpm). The resulting spray powder had an ignition loss of 31.5% by weight (ignite at 600° C. under air for 3 h) and a $d_{50}$ of 19.7 µm ($d_{10}$=3.19 µm, $d_{90}$=51.49 µm).

3. Preparation of the Shaped Multimetal Oxide Catalyst Bodies

Starting composition 1 was mixed homogeneously with starting composition 2 in the amounts required for a multimetal oxide active composition of stoichiometry $$[Bi_2W_2O_9 \cdot 2WO_3]_{0.48}[Mo_{12}Co_{5.4}Fe_{3.1}Si_{1.5}K_{0.08}O_x]_1$$

(total amount: 3 kg) in an Eirich intensive mixer (R02, fill volume: 3-5 l, power: 1.9 kW, Maschinenfabrik Gustav Eirich GmbH & Co KG, D-74736 Hardheim) with bladed heads rotating counter to the table (table speed: 50 rpm, bladed head speed: 2500 rpm) within 5 min.

To this end, based on the aforementioned overall composition, 1% by weight of the particular graphite were additionally admixed homogeneously at a speed of 30 rpm within 30 min in a drum hoop mixer (wheel diameter: 650 mm, drum volume: 5 l). The resulting mixture was then compacted in a laboratory calender with 2 counter-running steel rollers at a pressure of 9 bar and forced through a screen with a mesh size of 0.8 mm. The resulting compactate had a hardness of 10 N and an essentially uniform particle size of ≥0.4 mm and ≤0.8 mm.

The compactate was subsequently mixed with, based on its weight, a further 2.5% by weight of the same graphite in each case in a drum hoop mixer (wheel diameter: 650 mm, drum volume: 5 l) at a speed of 30 rpm within 30 minutes, and then compacted in a Kilian tableting press (9-tablet tableting machine) of the S100 type (from Kilian, D-50735 Cologne) under a nitrogen atmosphere to give annular shaped unsupported catalyst precursor bodies of geometry (5×3×2 mm, E (external diameter)×H (height)×I (internal diameter)) with a side crushing strength of 20±1 N (fill height: 7.5-9 mm, pressing force: 3.0-3.5 kN).

For the final thermal treatment, in each case 1000 g of the shaped unsupported catalyst precursor bodies prepared in each case, divided uniformly between 4 meshes arranged alongside one another with a square surface area of in each case 150 mm×150 mm (bed height: approx. 15 mm) were heated in a forced-air oven flowed through with 1000 l (STP)/h of air (from Heraeus Instruments GmbH, D-63450 Hanau, K 750/2) from room temperature (25° C.) to 185° C. initially with a heating rate of 80° C./h. This temperature was maintained for 1 h and then increased to 225° C. with a heating rate of 48° C./h. The 225° C. was maintained for 2 h before it was increased to 270° C. with a heating rate of 120° C./h. This temperature was likewise maintained for 1 h before it was increased to 464° C. with a heating rate of 60° C./h. This end temperature was held for 10 hours. The oven was then cooled to room temperature.

4. Testing of the Shaped Unsupported Catalyst Bodies, Obtained in Each Case with the Different Graphites, for the Heterogeneously Catalyzed Partial Oxidation of Propene to Acrolein A reaction tube (V2A steel; external diameter 21 mm, wall thickness 3 mm, internal diameter 15 mm, length 120 cm) was charged from the top downward in flow direction as follows:
Section 1: length approx. 30 cm
  40 g of steatite spheres with a diameter of from 1.5 to 2.0 mm as a preliminary bed.
Section 2: length approx. 70 cm
  Catalyst charge with 100 g of the annular unsupported catalyst prepared under 3.

The reaction tube was heated by means of a nitrogen-sparged salt bath.

The reactor was charged continuously with a charge gas mixture (mixture of air, polymer grade propylene and nitrogen) of the composition:
  5% by volume of propene,
  9.5% by volume of oxygen and,
as the remainder to 100% by volume, $N_2$, and the loading of the reaction tube with charge gas mixture was 100 l (STP)/h (5 l (STP)/h of propene) and the reaction tube was thermostatted by varying the salt bath temperature $T_S$ (° C.) such that the propene conversion C (mol %) in single pass of the charge gas mixture through the reaction tube was continuously about 95 mol %.

The graphites used and their particle properties were:

| Graphite | $d_{10}$ (µm) | $d_{50}$ (µm) | $d_{90}$ (µm) | $O_G$ (m²/g) |
|---|---|---|---|---|
| C1 Timrex HSAG 100[a] | 3.3 | 13.1 | 78.4 | 121 |
| C2 Asbury 230U[b] | 4.8 | 14.5 | 40.6 | 6.2 |
| C3 Timrex T44[a] | 6.4 | 20.8 | 56.8 | 6.5 |
| E1 Asbury 3160[b] | 37.0 | 123 | 259 | 1.6 |
| E2 Asbury 4012[b] | 87.6 | 166 | 270 | 1.7 |

[a]Graphites from Timcal Ltd., 6743 Bodio, Switzerland
[b]Graphites from Asbury Graphite Mills, Inc. New Jersey 08802, USA The different graphites used had the following properties (a dash means that no property determination was carried out):

| | Graphite | Ash content (% by weight) | $T_i$ (° C.) | $T_m$ °(C) |
|---|---|---|---|---|
| C1 | C1 | — | — | — |
| C2 | C2 | 0.3 | — | — |
| C3 | C3 | 0.1 | 505 | 670 |
| E1 | E1 | 0.7 | 505 | 700 |
| E2 | E2 | 0.2 | 550 | 745 |

FIG. 1 shows the particular particle diameter distribution for the different graphites used (laser, Malvern).

In this figure, the abscissa shows the diameter [µm] on a logarithmic scale. The ordinate shows the volume fraction of the particular graphite which has the particular diameter or a smaller diameter [% by volume].

In this figure:
-□- is C3
-▲- is C2
-○- is C1
-●- is E1, and
-+- is E2

The ash content indicates the oxidic residue remaining in the case of complete combustion of the graphite (in % by weight, based on the weight of the amount of graphite combusted).

The table below shows, for the shaped catalyst bodies obtained when the different graphites were used, their total pore volume V (cm³/g), their specific surface area O (m²/g), the pore diameter $d^{max}$ (µm) of those pores which, in their entirety, make the greatest percentage contribution to the total pore volume V, the amount of graphite (calculated as pure carbon) Δm (% by weight, based on the amount of graphite present in 100 shaped catalyst precursor bodies) which vanishes therefrom during the thermal treatment of these shaped catalyst precursor bodies, the salt bath temperature $T_s$ (° C.) (in each case determined after an operating time of 60 h) required in each case for the propylene conversion of 95 mol % when they are used as the catalyst for the described partial oxidation of propene to acrolein, the selectivity $S^A$ of acrolein formation (mol %), and the sum, which is important in the case of a subsequent partial oxidation of the acrolein formed to acrylic acid, of the selectivity $S^A$ of acrolein formation and the selectivity $S^{AA}$ of acrylic acid by-product formation ($S^A + S^{AA}$, mol %):

| Graphite used | Δm | V | O | $d^{max}$ | $T_S$ | $S^A$ | $S^A + S^{AS}$ |
|---|---|---|---|---|---|---|---|
| C1 | 57 | 0.268 | 6.67 | 0.224 | 332 | 87.3 | 94.5 |
| C2 | 20 | 0.267 | 6.11 | 0.250 | 327 | 87.8 | 94.5 |
| C3 | 23 | 0.275 | 6.64 | 0.259 | 332 | 88.6 | 95.0 |
| E1 | 11 | 0.261 | 6.28 | 0.264 | 336 | 88.9 | 95.4 |
| E2 | 11 | 0.249 | 5.86 | 0.273 | 331 | 89.2 | 95.4 |

Figure 2:
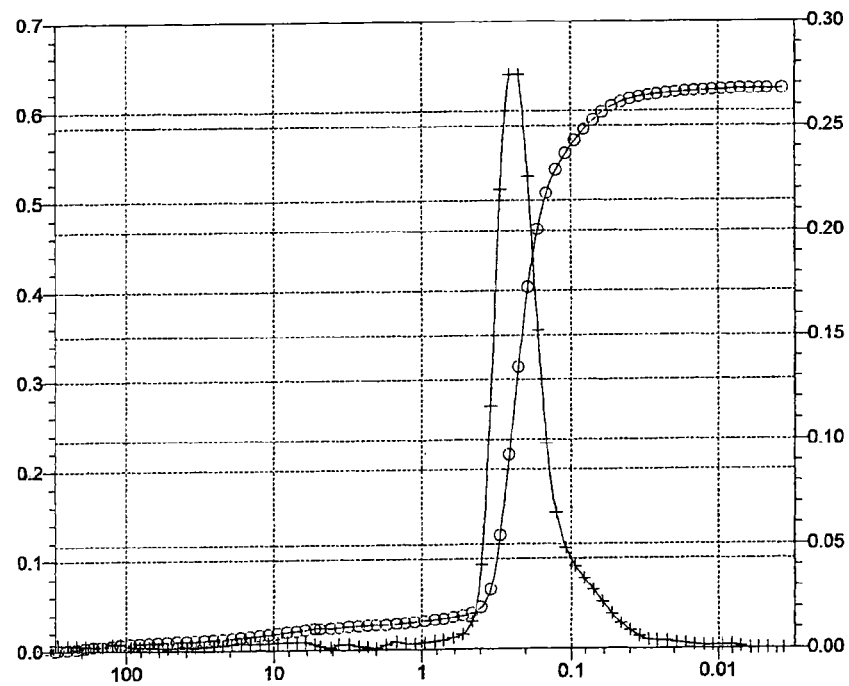
Figure 3:
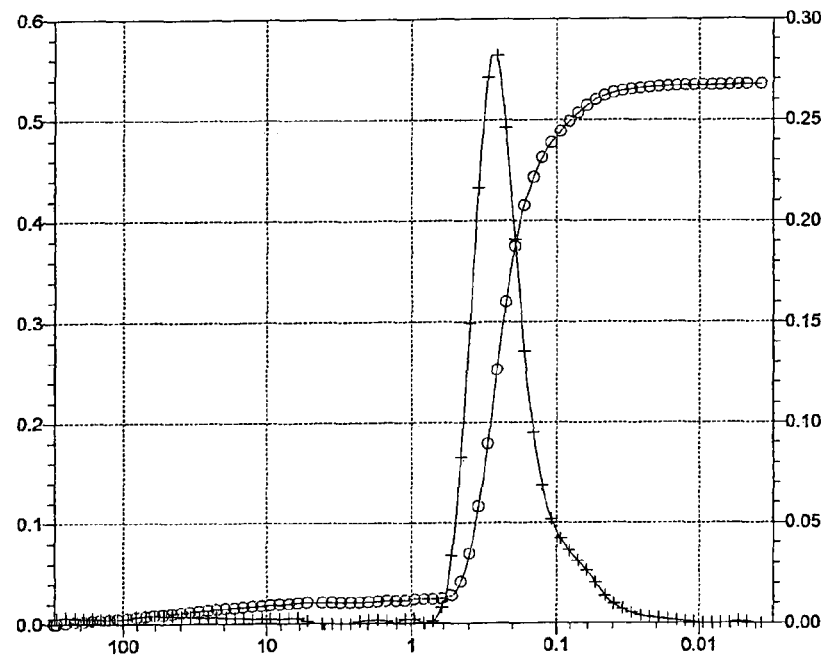
Figure 4:
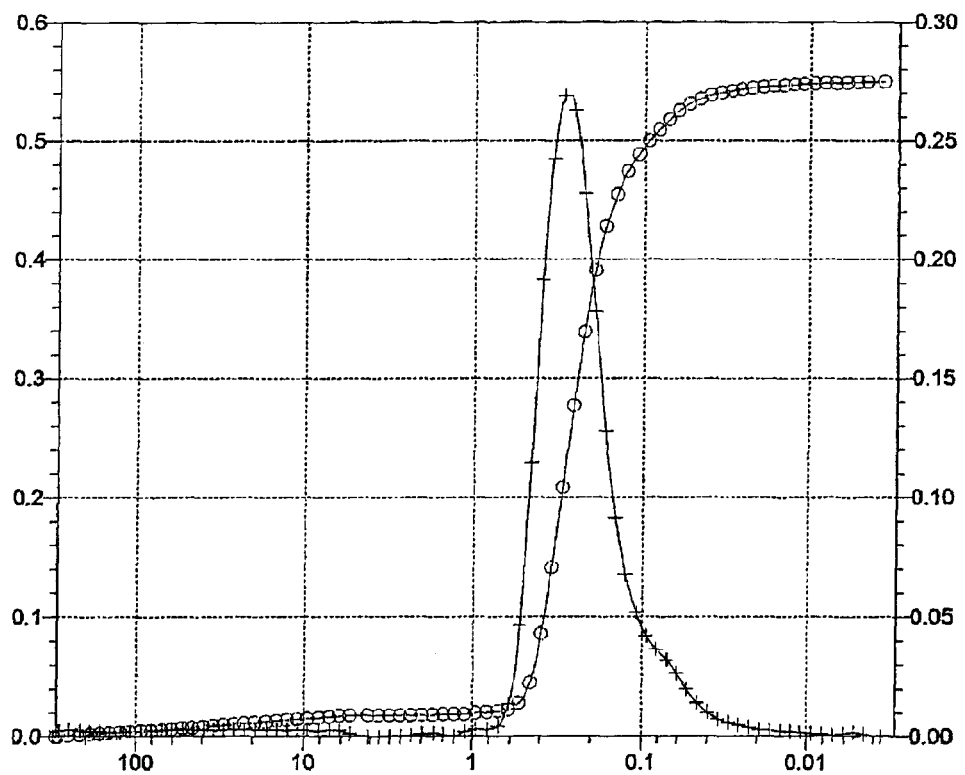
Figure 5:
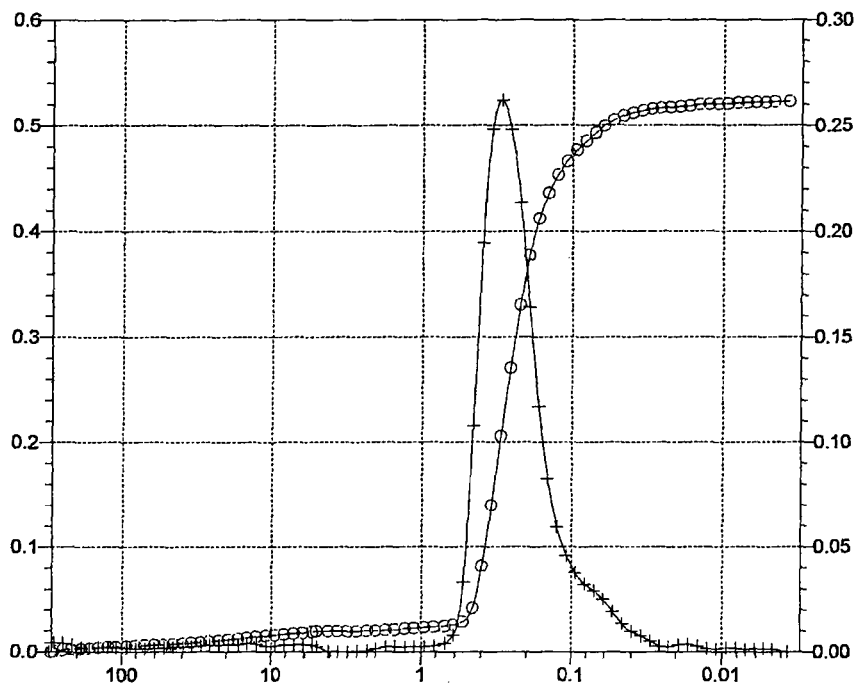
Figure 6:
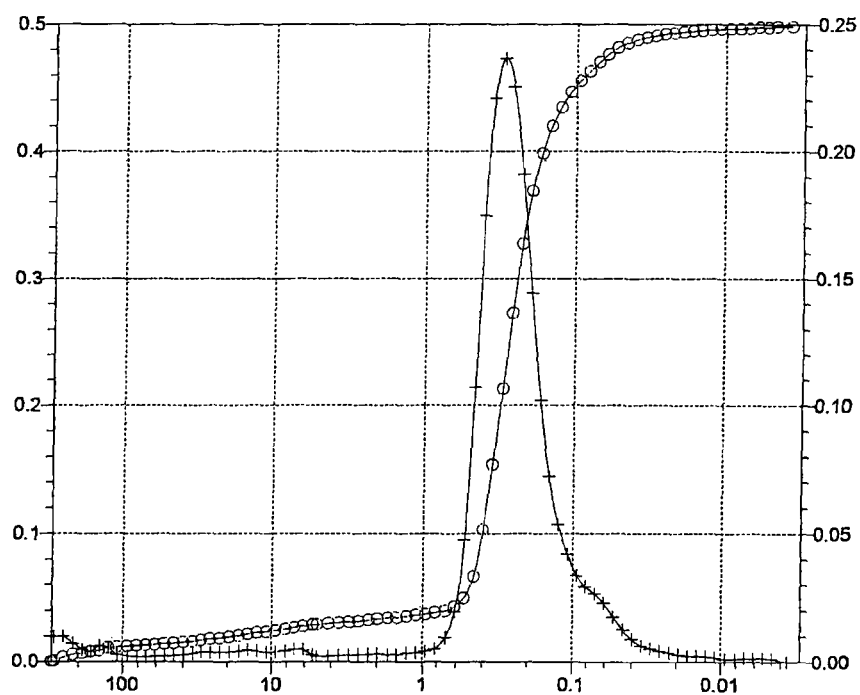

FIGS. 2 to 6 additionally show the pore distribution of the shaped unsupported catalyst bodies obtained with the different graphites (C1→FIG. 2; C2→FIG. 3; C3→FIG. 4; E1→FIG. 5; E2→FIG. 6). The pore diameter is in each case plotted on the abscissa in a logarithmic scale in μm. The logarithm of the differential contribution in ml/g of the particular pore diameter to the total pore volume is plotted on the left-hand ordinate (+ curve). The maximum indicates the pore diameter $d^{max}$ of those pores which make the greatest percentage contribution to the total pore volume. The integral over the individual contributions of the pores attributable to the individual pore diameters to the total pore volume is plotted on the right-hand ordinate in ml/g (O curve). The end point is in each case the total pore volume.

In the case of a preparation of the shaped catalyst bodies to be prepared as described above on the industrial scale, essentially the following modifications will be undertaken in preparation section "3.":

Mixing:
Eirich intensive mixer (Maschinenfabrik Gustav Eirich GmbH Co KG, D-74736 Hardheim) with rotating bladed heads (speed: 3000 rpm, mixing time: 25 min).

Compacting:
K200/100 compactor with concave, fluted smooth rollers (gap width: 2.8 mm, screen width: 1.0 mm, undersize screen width: 400 μm, target compressive force: 75 kN, screw speed: <70 rpm, from Hosokawa Bepex GmbH, D-74211 Leingarten).

Tableting:
Kilian Rx 73 rotary tableting press (pressing force: 3-15 kN, from Kilian, D-50735 Cologne).

Calcination:
Instead of performing the thermal treatment as described, it can also be performed by means of a belt calcining apparatus as described in Example 1 of DE-A 100 46 957 (except that the bed height in the decomposition (chambers 1 to 4) is advantageously 44 mm with a residence time per chamber of 1.46 h, and, in the calcination (chambers 5 to 8), it is advantageously 130 mm with a residence time of 4.67 h); the chambers have a base area (with a uniform chamber length of 1.40 m) of 1.29 m² (decomposition) and 1.40 m² (calcination) and are flowed through from below through the coarse-mesh belt by 50-150 m³ (STP)/h of forced air; in addition, the air is circulated by rotating ventilators (from 900 to 1500 rpm). Within the chambers, the temporal and local deviation of the temperature from the target value is always ≤2° C. Otherwise, the procedure is as described in Example 1 of DE-A 100 46 957.

The resulting shaped catalyst bodies are equally suitable as catalysts for the described partial oxidation of propylene to acrolein.

B) Preparation and testing of annular shaped unsupported catalyst bodies with the following stoichiometry of the active composition and using different graphites as shaping assistants (the reactants used were the chemicals already specified under A)):

$Mo_{12}Co_7Fe_{2.94}Bi_{0.6}Si_{1.59}K_{0.08}O_x$

At 60° C., 213 kg of ammonium heptamolybdate tetrahydrate (81.5% by weight of $MoO_3$) were dissolved in 600 l of water. While maintaining the 60° C., 0.97 kg of a 46.8% by weight aqueous potassium hydroxide solution of 20° C. was stirred into this solution (to obtain a solution A).

A second solution B was prepared by adding, at 60° C., 119.6 kg of an aqueous iron(III) nitrate nonahydrate melt (13.8% by weight of Fe) at 60° C. with stirring to 331.0 kg of an aqueous cobalt(II) nitrate solution (12.5% by weight of Co). After the addition had ended, stirring was continued at 60° C. for another 30 min. Thereafter, 112.3 kg of an aqueous bismuth nitrate solution (11.2% by weight of Bi) at 20° C. was stirred in at 60° C. to obtain solution B. Within 30 min, solution B was stirred into solution A at 60° C. 15 min after the stirring-in had ended, 18.26 kg of silica sol (49.1% by weight of $SiO_2$) were added at 60° C. to the slurry obtained. While maintaining the 60° C., stirring was continued for another 15 min. The resulting slurry was then spray-dried in a hot air countercurrent process (gas inlet temperature: 400±10° C., gas outlet temperature: 140±5° C.) to obtain a spray powder whose ignition loss (3 h at 600° C. under air) was 30% of its weight. The resulting spray powder had a particle diameter $d_{50}$ of 20.3 μm, a $d_{10}$ of 3.24 μm and a $d_{90}$ of 53.6 μm.

An additional 1.5% by weight in each case (based on the amount of spray powder) of the particular finely divided graphite was mixed into portions of the resulting spray powder.

The dry mixture resulting in each case was coarsened by means of a K200/100 compacter from Hosokawa Bepex GmbH (D-74211 Leingarten) under the conditions of gap width 2.8 mm, screen width 1.0 mm, undersize screen width 400 μm, target compression force 60 kN and screw speed 65 to 70 rpm, by precompaction to an essentially uniform particle size of from 400 μm to 1 mm. The compactate had a hardness of 10 N.

The compactate was subsequently mixed with, based on its weight, a further 2% by weight of the same graphite in each case and then compacted in a Kilian Rx73 rotary tableting press (tableting machine) from Kilian, D-50735 Cologne, under a nitrogen atmosphere to give annular shaped unsupported catalyst precursor bodies with uncurved top surface of geometry 5 mm×3 mm×2 mm (E×H×I) with a side crushing strength of 20±1 N.

For the final thermal treatment, in each case 1900 g of the shaped unsupported catalyst precursor bodies were poured into a heatable forced-air chamber (capacity 0.12 m³) (2 m³ (STP) of air/min). Subsequently, the temperature in the bed was changed as follows:

increased from 25° C. to 160° C. at 1° C./min;
then held at 160° C. for 100 min;
then increased from 160° C. to 200° C. at 3° C./min;
then held at 200° C. for 100 min;
then increased from 200° C. to 230° C. at 2° C./min;

then held at 230° C. for 100 min;
then increased from 230° C. to 270° C. at 3° C./min;
then held at 270° C. for 100 min;
then increased to 380° C. at 1° C./min;
then held at 380° C. for 4.5 h;
then increased to 430° C. at 1° C./min;
then held at 430° C. for 4.5 h;
then increased to 500° C. at 1° C./min;
then held at 500° C. for 9 h;
then cooled to 25° C. within 4 h.

This afforded annular shaped unsupported catalyst bodies from the annular shaped unsupported catalyst precursor bodies.

(Instead of performing the thermal treatment as described, it can also be performed by means of a belt calcining apparatus as described in Example 3 of DE-A 100 46 957; the chambers have a base area (with a uniform chamber length of 1.40 m) of 1.29 m² (decomposition chambers 1-4) and 1.40 m² (calcination chambers 5-8) and are flowed through from below through the coarse-mesh belt by 70-120 m³ (STP)/h of forced air, preferably by 75 m³ (STP)/h of forced air; in addition, the air is circulated by rotating ventilators (from 900 to 1500 rpm); within the chambers, the temporal and local deviation of the temperature from the target value is always ≤2° C.; the annular shaped unsupported catalyst precursor bodies are conducted through the chambers in a bed height of from 50 mm to 110 mm, preferably from 50 mm to 70 mm; otherwise, the procedure is as described in Example 3 of DE-A 100 46 957; the resulting annular unsupported catalysts can be used like the shaped unsupported catalyst bodies obtained in A) for the catalytic partial oxidation of propene to acrolein in the gas phase described in A) 4.)

The resulting annular unsupported catalysts were used as described in A) 4. as catalysts for a heterogeneously catalyzed partial gas phase oxidation of propene to acrolein (but with the difference that the preliminary bed in the reaction tube consisted for a length of 30 cm of steatite rings of geometry 5 mm×3 mm×2 mm (E×H×I) and for a bed length of 70 cm of the shaped unsupported catalyst bodies).

The resulting selectivities SA of acrolein formation (likewise after 120 h of operating time) were:

| Graphite used | $S^A$ (mol %) |
| --- | --- |
| C1 | 89.8 |
| C2 | 89.9 |
| C3 | 90.5 |
| E1 | 90.8 |
| E2 | 91.0 |

C) Preparation and testing of annular shaped unsupported catalyst bodies with the following stoichiometry of the active composition and using different graphites as shaping assistants:

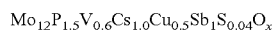

$Mo_{12}P_{1.5}V_{0.6}Cs_{1.0}Cu_{0.5}Sb_1S_{0.04}O_x$ 537.5 kg of ammonium heptamolybdate tetrahydrate $((NH_4)_6Mo_7O_{24}\cdot 4H_2O$ (81% by weight of $MoO_3$, 8% by weight of $NH_3$, ≤50 ppm by weight of Na and ≤100 ppm by weight of K)) were metered with stirring (70 revolutions per minute (rpm)) into 619 l of water heated to 45° C. in a water-heated jacketed vessel. This lowered the temperature of the solution to 37° C. In order to ensure reliable dissolution of the ammonium heptamolybdate, stirring was continued for another 15 minutes after the end of the metered addition, while retaining the temperature of 37° C. With further stirring at the same temperature, 17.82 g of ammonium metavanadate ($NH_4VO_3$, 77% by weight of $V_2O_5$, 14.5% by weight of $NH_3$, ≤150 ppm by weight of Na and ≤500 ppm by weight of K) were metered in within 3 minutes. Stirring was continued for 2 minutes. Then, a colorless clear solution of 49.6 kg of cesium nitrate ($CsNO_3$ with 72% by weight of $Cs_2O$ and ≤50 ppm by weight of Na, ≤100 ppm by weight of K, ≤10 ppm by weight of Al and ≤20 ppm by weight of Fe) at 60° C., prepared in a separate dissolution vessel, was stirred into 106 l of water within one minute. In the course of this, the temperature of the resulting suspension rose to 39° C. After continuing to stir for one minute, 31.66 l of 75% by weight phosphoric acid (density at 25° C. and 1 atm: 1.57 g/ml, viscosity at 25° C. and 1 atm: 0.147 cm²/S) were metered in within a further minute with continued stirring. Owing to the exothermic reaction, the temperature rose to 42° C. Stirring was again continued for 1 minute. Then, 1.34 kg of ammonium sulfate (($NH_4)_2SO_4$ (>99% by weight)) were stirred in within one minute and the mixture was stirred for a further 1 minute. With continued stirring at identical temperature, 37.04 kg of antimony trioxide ($Sb_2O_3$, particle diameter $d_{50}$=approx. 2 μm, crystal structure according to XRD: >75% senarmontite, <25% valentinite, purity: >99.3% by weight, ≤0.3% by weight of $As_2O_3$, ≤0.3% by weight of PbO and ≤300 ppm by weight of FeO) were added within 3 minutes (commercially available as Triox White, Code No. 639000 from Antraco, D-10407 Berlin). The stirrer speed was then reduced from 70 to 50 rpm. Subsequently, the stirred suspension was heated to 95° C. in a linear manner within 30 minutes by means of steam in the jacket. At this temperature and 50 rpm, 51.64 kg of copper nitrate solution (aqueous $Cu(NO_3)_2$ solution with 15.6% by weight of Cu) were added within 4 minutes. After continuing to stir at 95° C. for four minutes, the stirrer speed was reduced further from 50 to 35 rpm. Subsequently, the entire suspension was discharged within 4 minutes into a nitrogen-blanketed spray tower reservoir vessel heated to 85° C. and stirred at 35 rpm, and was flushed in with 20 l of water (25° C.). From this vessel, the suspension was spray-dried in a rotary disk spray tower in countercurrent with an inlet temperature of 285° C. and an outlet temperature of 110° C. within 3.5 h, and the resulting spray powder had an ignition loss (1 h at 500° C. in air) of approx. 16% by weight.

The spray powder was mixed homogeneously with 1.5% by weight of the particular graphite and compacted (K200/100 compactor with concave, fluted, smooth rollers from Hosokawa Bepex GmbH, D-74211 Leingarten, gap width: 2.8 mm, screen width: 1.25 mm, undersize screen width: 400 μm, screw speed: 65 to 70 rpm). For the tableting, a further 1% by weight of the same graphite in each case was mixed into the compactate. Subsequently, the compactate was tabletted in a Kilian rotary tableting press (Rx73 tableting machine from Kilian, D-50735 Cologne) under a nitrogen atmosphere to give annular four-ring tablets of geometry 7 mm×7 mm×3 mm (external diameter×height×internal diameter) with a side crushing strength of 35±2 N.

8 kg of the untreated tablets were distributed uniformly in a wire vessel of base area 33.0 cm×49.5 cm, giving a bed height of 4 cm. The wire vessel was disposed in a chamber oven (from Elino Industrie-Ofenbau, Carl Hanf GmbH & Co, D-52355 Duren, model KA-040/006-08 EW.OH, dimensions: length=57 cm, width=57 cm, height=80 cm) such that the bed of the tablets could be flowed through uniformly. 2 m³ (STP)/h of fresh air were supplied and the air circulation in the oven was adjusted such that the bed was flowed through at a speed of 0.9 m/s (determined by means of Aerometer, from Testo, model 445). The oven was then heated to 380° C. with the following temperature ramp: heat to 180° C. within 40 min, hold for 30 min, heat to 220° C. within 10 min, hold for 30 min, heat to 270° C. within 13 min, hold for 30 min, heat to 340° C. within 25 min and then to 380° C. within 40 min. This temperature was then held for 390 min. During this, the NH$_3$ content in the thermal treatment atmosphere sucked out was monitored continuously by FTIR spectroscopy ("Impact" spectrometer from Nicolet, stainless steel IR cell with CaF$_2$ window, layer thickness 10 cm, heating to 120° C., determination of the concentration with reference to the intensity of the band at 3.333 cm$^{-1}$). The NH$_3$ content remained ≤2.4% by volume over the entire thermal treatment. This maximum value was attained at 220° C. The annular shaped catalyst bodies thus obtained all had a side crushing strength of 15±2 N, an ammonium content (determined by Kjeldahl tritration) of 0.6% by weight of NH$_4^+$ and an MoO$_3$ content of 1 XRD intensity %. The latter is calculated as the ratio of the intensity of the (021) MoO$_3$ reflection at 2Θ=27.3° to the intensity of the (222) reflection of the heteropoly compound at 2Θ=26.5° C. in the X-ray powder diffractogram (with Cu—Kα radiation).

(Alternatively to the calcination in the chamber oven described, the calcination can also be effected here in a belt calciner as described in A).)

To test the annular unsupported catalysts, obtained in each case, for a heterogeneously catalyzed partial oxidation of methacrolein to methacrylic acid, in each case 2 kg of the annular shaped catalyst bodies thus prepared were charged with a preliminary bed and a downstream bed of 50 g of steatite rings in each case (steatite C220 from CeramTec) of geometry 7 mm×7 mm×4 mm (external diameter×height× internal diameter) in a stainless steel model tube (external diameter=30 mm, internal diameter=26 mm, length=4.15 m) (fill height: 397 cm). This was disposed in a nitrogen-sparged salt bath heated to 287° C. The catalytic testing was effected in cycle gas mode: the reactor exit gas was conducted through a Venturi nozzle, quenched there with water at 75° C. and then passed into the bottom of the distillation column A heated to 75° C. Approx. 55 kg/day of a mixture of reaction product and water (typically approx. 9.5% by weight of methacrylic acid, approx. 0.8% by weight of acetic acid and approx. 0.1% by weight of acrylic acid in water) were withdrawn here. The depleted gas stream passed into column A. A substream was withdrawn in the middle thereof and passed at the bottom into a column B heated to 7° C. A solution of 6% by weight of hydroquinone in water (2 kg/h) fed in at the top of column B was used to free the offgas of the remaining organic components in this column, and it escaped at the top of the column. The contents of the bottom of column B (essentially approx. 1.4% by weight of methacrolein in water) were pumped to the top of column A; there, an additional 220 g/h of acrolein were fed in. At the top of column A, at a top temperature of 66° C., 1700 l (STP)/h of cycle gas were withdrawn, mixed with 450 l (STP)/h of fresh air and passed into the reactor as reactant gas which comprised approx. 5% by volume of methacrolein, approx. 12% by volume of O$_2$, approx. 21% by volume of steam, approx. 2.5% by volume of CO, approx. 3% by volume of CO$_2$ and further inert gas (essentially nitrogen). This gave rise to a weight hourly space velocity (WHSV) of 0.17 h$^{-1}$.

During the 5-day testing, the methacrolein conversion in single pass was kept at 65 mol %; to this end, the salt bath temperature was increased stepwise.

On the 5th day in each case, the following selectivities S$^{MA}$ of methacrylic acid formation were obtained as a function of the graphite used:

| Graphite | S$^{MA}$ (mol %) |
|---|---|
| C1 | 85.4 |
| C2 | 85.2 |
| C3 | 85.6 |
| E1 | 86.0 |
| E2 | 86.2 |

D) Preparation and testing of annular shaped unsupported catalyst bodies with a multimetal oxide active composition comprising vanadium, phosphorus, iron and oxygen and using different graphites as shaping assistants A nitrogen-inertized 8 m$^3$ steel/enamel stirred tank which was externally heatable by means of pressurized water and had baffles was initially charged with 4602 kg of isobutanol. After the three-level impeller stirrer had been switched on, the isobutanol was heated to 90° C. under reflux. At this temperature, the addition of 690 kg of vanadium pentoxide was then commenced by means of a conveying screw. After about ⅔ of the desired amount of vanadium pentoxide had been added after approx. 20 minutes, the pumped addition of 805 kg of polyphosphoric acid having a P$_2$O$_5$ content of 76% by weight (corresponds to 105% by weight of H$_3$PO$_4$) and a temperature of 50° C. was commenced with further addition of vanadium pentoxide. After the addition of the phosphoric acid had ended, the reaction mixture was heated under reflux to about 100 to 108° C. and left under these conditions for 14 hours. Thereafter, the hot suspension was cooled to 60° C. within 70-80 minutes and 22.7 kg of Fe(III) phosphate (29.9% by weight of Fe) were added. After heating to reflux again within 70 minutes, the suspension boiled under reflux for a further hour. Subsequently, the suspension was discharged into a pressure suction filter which had been inertized with nitrogen and heated beforehand, and filtered off at a temperature of about 100° C. at a pressure above the suction filter of up to 0.35 MPa abs. The filtercake was blown dry by constantly introducing nitrogen at 100° C. with stirring with a height-adjustable stirrer disposed in the middle within about one hour. The blowing to dryness was followed by heating to approx. 155° C. and evacuation to a pressure of 15 kPa abs (150 mbar abs). The drying was carried out down to a residual isobutanol content of <2% by weight in the dried catalyst precursor composition.

The FeN ratio was 0.016.

Subsequently, the dried powder was treated in a rotary tube with a length of 6.5 m, an internal diameter of 0.9 m and internal spiral helices (for mixing purposes) under air for 2 hours. The speed of the rotary tube was 0.4 rpm. The powder was conveyed into the rotary tube in an amount of 60 kg/h. The air feed was 100 m$^3$/h. The temperatures, measured directly on the outside of the externally heated rotary tube, of the five heating zones of equal length were, in the direction from "outlet of the powder" to "inlet of the powder" of the rotary tube, 250° C., 300° C., 345° C., 345° C. and 345° C.

The precursor composition withdrawn from the rotary tube was mixed intimately and homogeneously with 1% by weight of the particular graphite in a drum loop mixer. The resulting mixture was then compacted in a laboratory calender with 2 counter-running steel rollers at a pressure of 9 bar and forced through a screen with a mesh size of 0.8 mm. The resulting compactate had an essentially uniform particle size of ≥0.4 mm and ≤0.8 mm. It was mixed with a further 2% by weight of the particular graphite in a drum loop mixer, and tabletted in a tabletting machine (Kilian LX 18 tabletting machine (from Kilian, D-50735 Cologne), compression force 5.3 N) to 5×3.2×2.5 mm hollow cylinders (external diameter×height× diameter of the inner hole). These had a side crushing strength of 11 N.

The resulting 5×3.2×2.5 mm (E×H×I) hollow cylinders were calcined according to WO 03/78059, page 39, under Example 9, to give the particular shaped catalyst bodies.

For the purpose of testing the shaped catalyst bodies obtained in each case as catalysts in a process for heterogeneously catalyzed partial gas phase oxidation of n-butane for the preparation of maleic anhydride, an experimental plant which was equipped with a feed unit and a tube bundle reactor unit was used. The plant was operated in straight pass, as described in EP-B1 261 424.

The hydrocarbon was added via a pump in liquid form under quantitative control. The oxygenous gas added was air under quantitative control. Triethyl phosphate (TEP) was likewise added in liquid form, dissolved in water, under quantitative control.

The tube bundle reactor unit consisted of a tube bundle reactor with one reactor tube. The length of the stainless steel reactor tube was 6.5 m, the internal diameter 22.3 mm, the wall thickness 2.3 mm. Within the reactor tube, a multithermoelement with 20 temperature measuring points was disposed in an axially centered protective tube with external diameter 6 mm. The reactor tube was heated by a heat carrier circuit with a length of 6.5 m. The heat carrier medium used was a salt melt.

The reactor tube was flowed through by the reaction gas mixture from the top downward. The upper 0.2 m of the 6.5 m-long reactor tube remained unfilled. This was followed by a 0.3 m-long preheating zone which was filled with shaped steatite bodies of steatite C220 of geometry 5×3.2×2 mm (E×H×I) as inert material. The preheating zone was followed by the catalyst bed which comprised a total of 2180 ml of catalyst in each case.

Directly downstream of the tube bundle reactor unit, gaseous product was withdrawn and sent to online gas chromatography analysis. The main stream of the gaseous reactor effluent was discharged from the plant.

The composition of the charge gas mixture was

| | |
|---|---|
| 2% by volume of | n-butane, |
| 3% by volume of | H$_2$O, |
| 2.25 ppm by volume of | TEP and, | as the remainder, air.

The inlet pressure was 3.3 bar. The total loading of the fixed catalyst bed (pure inert material sections are not included) was 2000 l (STP)/(l·h); the salt bath temperature (approx. 415° C.) was in each case adjusted such that the butane conversion, based on single pass, was 85 mol %.

After an operating time of the experimental plant of 150 h in each case, the selectivity of maleic anhydride formation $S^{MAH}$ was determined.

The values as a function of the graphite used were as follows:

| Graphite | $S^{MAH}$ (mol %) |
|---|---|
| C1 | 56.9 |
| C2 | 56.8 |
| C3 | 57.1 |
| E1 | 57.5 |
| E2 | 57.4 |

U.S. Provisional Patent Application No. 60/885,701, filed Jan. 19, 2007, and No. 60/886,757, filed Jan. 26, 2007, are incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

The invention claimed is:

1. A process for preparing shaped catalyst bodies whose active composition is a multielement oxide, in which a finely divided precursor mixture which comprises added graphite as a finely divided shaping assistant is shaped to the desired geometry and the resulting shaped catalyst precursor bodies are treated thermally at elevated temperature to obtain the shaped catalyst bodies whose active composition is a multi-element oxide, wherein a) for the specific surface area $O_G$ of the finely divided graphite:

$$0.5 \text{ m}^2/\text{g} \leq O_G \leq 5 \text{ m}^2/\text{g}$$

and b) for the particle diameter $d_{50}$ of the finely divided graphite:

$$40 \text{ μm} \leq d_{50} \leq 200 \text{ μm}.$$

2. The process according to claim 1, wherein, for the finely divided graphite:

$$60 \text{ μm} \leq d_{50} \leq 200 \text{ μm}.$$

3. The process according to claim 1, wherein, for the finely divided graphite:

$$90 \text{ μm} \leq d_{50} \leq 200 \text{ μm},$$

$$20 \text{ μm} \leq d_{10} \leq 90 \text{ μm, and}$$

$$150 \text{ μm} \leq d_{90} \leq 300 \text{ μm}.$$

4. The process according to claim 1, wherein the finely divided precursor mixture, based on its total weight, comprises from 0.1 to 35% by weight of the added finely divided graphite.

5. The process according to claim 1, wherein the thermal treatment of the shaped catalyst precursor bodies until the shaped catalyst bodies are obtained converts from 1 to 70% by weight of the graphite present in the shaped catalyst precursor bodies to compounds which escape in gaseous form.

6. The process according to claim 1, wherein the thermal treatment of the shaped catalyst precursor bodies is effected in oxidizing atmosphere.

7. The process according to claim 1, wherein the thermal treatment of the shaped catalyst precursor bodies is effected at temperatures of from 150 to 650° C.

8. The process according to claim 1, wherein the thermal treatment of the shaped catalyst precursor bodies is effected in an air stream.

9. The process according to claim 1, wherein the finely divided graphite is natural graphite.

10. The process according to claim 1, wherein the finely divided graphite has a temperature T, at the start of combustion which is at least 50° C. greater than the highest temperature which is effective for a period of at least 30 minutes on the shaped catalyst bodies in the course of the thermal treatment.

11. The process according to claim 10, wherein T, of the finely divided graphite is ≥500° C.

12. The process according to claim 11, wherein the maximum combustion temperature $T_m$ of the finely divided graphite is $\geq 680°$ C.

13. The process according to claim 1, wherein the particle diameters of the finely divided precursor mixture, excluding the added shaping assistant, are in the range from 10 to 2000 μm.

14. The process according to claim 1, wherein the shaping to the desired geometry is effected by tableting.

15. The process according to claim 1, wherein the shaping is effected using a shaping pressure of from 50 kg/cm² to 5000 kg/cm².

16. The process according to claim 1, wherein the shaped catalyst body is a sphere having a diameter of from 2 to 10 mm.

17. The process according to claim 1, wherein the shaped catalyst body is a solid cylinder whose external diameter and length are from 2 to 10 mm.

18. The process according to claim 1, wherein the shaped catalyst body is a ring whose external diameter and length are from 2 to 10 mm and whose wall thickness is from 1 to 3 mm.

19. The process according to claim 1, wherein the active composition is a multimetal oxide.

20. The process according to claim 1, wherein the active composition is a multielement oxide which comprises
   a) the elements Mo, Fe and Bi, or
   b) the elements Mo and V, or
   c) the elements Mo, V and P, or
   d) the elements V and P.

21. A shaped catalyst body obtainable by a process according to claim 1.

22. A process comprising conducting a heterogeneously catalyzed gas phase reaction, wherein the catalyst used comprises at least one shaped catalyst body according to claim 21.

23. The process according to claim 22, wherein the heterogeneously catalyzed gas phase reaction is a heterogeneously catalyzed partial oxidation of an organic compound.

24. The process according to claim 23, wherein the heterogeneously catalyzed partial oxidation is the partial oxidation of propene to acrolein and/or acrylic acid.

25. The process according to claim 23, wherein the heterogeneously catalyzed partial oxidation is the partial oxidation of propane to acrolein and/or acrylic acid.

26. The process according to claim 23, wherein the heterogeneously catalyzed partial oxidation is the partial oxidation of isobutene or tert-butanol to methacrolein.

27. The process according to claim 23, wherein the heterogeneously catalyzed partial oxidation is the partial oxidation of methacrolein to methacrylic acid.

28. The process according to claim 23, wherein the heterogeneously catalyzed partial oxidation is the partial oxidation of acrolein to acrylic acid.

29. The process according to claim 23, wherein the heterogeneously catalyzed partial oxidation is the partial oxidation of a hydrocarbon having at least 4 carbon atoms to maleic anhydride.

* * * * *